(12) United States Patent
Cauvin et al.

(10) Patent No.: US 10,940,099 B2
(45) Date of Patent: Mar. 9, 2021

(54) PITUITOUS SILICONE EMULSIONS

(71) Applicant: Dow SILICONES Corporation, Midland, MI (US)

(72) Inventors: Severine Cauvin, Mons (BE); Patrick J. Fryfogle, Midland, MI (US); Sophie Hanssens, Chastre (BE); Donald Kadlec, Midland, MI (US); Stephane Ugazio, Soignies (BE); Marine Viaud, Talence (FR); Brett Lee Zimmerman, Frankenmuth, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/544,432

(22) PCT Filed: Apr. 4, 2016

(86) PCT No.: PCT/US2016/025839
§ 371 (c)(1),
(2) Date: Jul. 18, 2017

(87) PCT Pub. No.: WO2016/164296
PCT Pub. Date: Oct. 13, 2016

(65) Prior Publication Data
US 2018/0078467 A1 Mar. 22, 2018

Related U.S. Application Data

(60) Provisional application No. 62/144,546, filed on Apr. 8, 2015.

(51) Int. Cl.
| | | |
|---|---|---|
| *C08J 3/03* | (2006.01) | |
| *A61K 8/06* | (2006.01) | |
| *C08L 83/14* | (2006.01) | |
| *A61Q 5/12* | (2006.01) | |
| *A61Q 19/00* | (2006.01) | |
| *A61K 8/895* | (2006.01) | |
| *A61K 8/25* | (2006.01) | |
| *A61Q 5/00* | (2006.01) | |
| *A61Q 5/02* | (2006.01) | |
| *C11D 3/00* | (2006.01) | |
| *C11D 3/12* | (2006.01) | |
| *C11D 3/37* | (2006.01) | |
| *C08G 77/50* | (2006.01) | |

(52) U.S. Cl.
CPC ............... *A61K 8/062* (2013.01); *A61K 8/25* (2013.01); *A61K 8/895* (2013.01); *A61Q 5/00* (2013.01); *A61Q 5/02* (2013.01); *A61Q 5/12* (2013.01); *A61Q 19/00* (2013.01); *C08J 3/03* (2013.01); *C08L 83/14* (2013.01); *C11D 3/001* (2013.01); *C11D 3/124* (2013.01); *C11D 3/373* (2013.01); *A61K 2800/21* (2013.01); *C08G 77/50* (2013.01); *C08J 2383/04* (2013.01); *C08J 2383/07* (2013.01)

(58) Field of Classification Search
CPC . C08J 3/03; C08L 83/14; C08G 77/50; C08G 77/08
See application file for complete search history.

(56) References Cited

U.S. PATENT DOCUMENTS

| | | |
|---|---|---|
| 2,798,053 A | 7/1957 | Brown |
| 2,857,356 A | 10/1958 | Goodwin |
| 3,159,601 A | 12/1964 | Ashby |
| 3,220,972 A | 11/1965 | Lamoreaux |
| 3,296,291 A | 1/1967 | Chalk et al. |
| 3,419,593 A | 12/1968 | Willing |
| 3,516,946 A | 6/1970 | Modic |
| 3,715,334 A | 2/1973 | Karstedt |
| 3,814,730 A | 6/1974 | Karstedt |
| 3,923,705 A | 12/1975 | Smith |
| 3,928,629 A | 12/1975 | Chandra et al. |
| 3,958,581 A | 5/1976 | Abegg et al. |
| 3,962,418 A | 6/1976 | Birkofer |
| 3,989,668 A | 11/1976 | Lee et al. |
| 4,009,256 A | 2/1977 | Nowak, Jr. et al. |
| 4,122,029 A | 10/1978 | Gee et al. |
| 4,165,336 A | 8/1979 | Bouillon et al. |
| 4,250,108 A | 2/1981 | Bouillon et al. |
| 4,290,974 A | 9/1981 | Bouillon et al. |
| 4,304,730 A | 12/1981 | Bouillon et al. |
| 4,323,549 A | 4/1982 | Bouillon et al. |

(Continued)

FOREIGN PATENT DOCUMENTS

| | | |
|---|---|---|
| EP | 0487404 | 5/1992 |
| EP | 0964023 | 12/1999 |
| FR | 2282426 | 3/1976 |
| FR | 2645148 | 10/1990 |

(Continued)

OTHER PUBLICATIONS

Search report from corresponding Japanese 2017-552121 application, dated Oct. 1, 2016.
Search report from corresponding Japan 2019229233 application, dated Nov. 30, 2020.

\* cited by examiner

*Primary Examiner* — Margaret G Moore

(57) ABSTRACT

The present invention provides methods for preparing emulsions of silicone fluids having pituitous rheological properties. The present invention also provides emulsions of a silicone fluid having pituitous rheological properties and composition comprising the emulsions. The compositions include, but are not limited to, personal care compositions and compositions for hair shampoo, hair conditioner, hair treatment composition, or skin care product.

18 Claims, 20 Drawing Sheets

(56) References Cited

U.S. PATENT DOCUMENTS

| | | |
|---|---|---|
| 4,327,031 A | 4/1982 | Bouillon et al. |
| 4,330,488 A | 5/1982 | Bouillon et al. |
| 4,387,089 A | 6/1983 | De Polo |
| 4,406,880 A | 9/1983 | Bouillon et al. |
| 4,489,057 A | 12/1984 | Welters et al. |
| 4,562,067 A | 12/1985 | Hopp et al. |
| 4,585,597 A | 4/1986 | Lang et al. |
| 4,704,272 A | 11/1987 | Oh et al. |
| 4,741,855 A | 5/1988 | Grote et al. |
| 4,761,454 A * | 8/1988 | Oba .................. C08J 3/122 524/588 |
| 4,775,526 A | 10/1988 | Lang et al. |
| 4,788,006 A | 11/1988 | Bolich, Jr. et al. |
| 5,036,117 A | 7/1991 | Chung et al. |
| 5,175,325 A | 12/1992 | Brown et al. |
| 5,236,986 A | 8/1993 | Sakuta |
| 5,387,417 A | 2/1995 | Rentsch |
| 5,573,709 A | 11/1996 | Wells |
| 5,599,808 A | 2/1997 | Goldstein et al. |
| 5,643,557 A | 7/1997 | Eteve et al. |
| 5,690,915 A | 11/1997 | Eteve et al. |
| 5,690,917 A | 11/1997 | Eteve et al. |
| 5,695,747 A | 12/1997 | Forestier et al. |
| 5,762,912 A | 6/1998 | Eteve |
| 5,788,955 A | 8/1998 | Eteve et al. |
| 5,795,565 A | 8/1998 | Eteve et al. |
| 5,811,487 A | 9/1998 | Schulz, Jr. et al. |
| 5,880,210 A | 3/1999 | Schulz, Jr. et al. |
| 5,919,441 A | 7/1999 | Mendolia et al. |
| 5,929,162 A | 7/1999 | Horne et al. |
| 5,948,395 A | 9/1999 | Le Bras-Roulier et al. |
| 5,981,680 A | 11/1999 | Petroff et al. |
| 6,013,682 A | 1/2000 | Dalle et al. |
| 6,075,087 A | 6/2000 | Juen et al. |
| 6,200,581 B1 | 3/2001 | Lin et al. |
| 6,239,378 B1 | 5/2001 | Shephard |
| 6,291,563 B1 | 9/2001 | Horne et al. |
| 6,306,992 B1 | 10/2001 | Yoshitake et al. |
| 6,420,504 B1 | 7/2002 | Yoshitake et al. |
| 6,423,322 B1 | 7/2002 | Fry |
| 6,605,734 B2 | 8/2003 | Roy et al. |
| 6,806,339 B2 * | 10/2004 | Cray .................. C08G 77/04 524/588 |
| 6,827,929 B1 | 12/2004 | Lord et al. |
| 6,916,464 B2 | 7/2005 | Hansenne et al. |
| 6,936,686 B2 | 8/2005 | Awad |
| 6,958,155 B2 | 10/2005 | Lu et al. |
| 6,987,157 B2 | 1/2006 | Clement et al. |
| 7,078,026 B2 | 7/2006 | Ferrari et al. |
| 7,202,320 B2 | 4/2007 | George et al. |
| 7,378,482 B2 | 5/2008 | Asch et al. |
| 7,429,636 B2 | 9/2008 | Asch et al. |
| 7,432,338 B2 | 10/2008 | Chapman et al. |
| 7,449,536 B2 | 11/2008 | Chapman et al. |
| 7,452,849 B2 | 11/2008 | Berry et al. |
| 7,462,669 B2 | 12/2008 | Osawa |
| 7,592,412 B2 | 9/2009 | Cray et al. |
| 7,649,071 B2 | 1/2010 | Schlitzer et al. |
| 7,803,358 B2 | 9/2010 | Gordan et al. |
| 7,887,786 B2 | 2/2011 | Tournilhac et al. |
| 8,012,544 B2 | 9/2011 | Liu |
| 8,017,712 B2 | 9/2011 | Berry et al. |
| 8,110,630 B2 | 2/2012 | Lin et al. |
| 8,273,840 B2 | 9/2012 | Lin |
| 8,728,500 B2 | 5/2014 | McDermott et al. |
| 8,920,783 B2 | 12/2014 | Lin |
| 9,504,748 B2 | 11/2016 | Cauvin et al. |
| 2003/0072730 A1 | 4/2003 | Tournilhac |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235552 A1 | 12/2003 | Yu |
| 2003/0235553 A1 | 12/2003 | Lu et al. |
| 2004/0115154 A1 | 6/2004 | Yu |
| 2004/0120912 A1 | 6/2004 | Yu |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2005/0112072 A1 | 5/2005 | Wang et al. |
| 2005/0287105 A1 | 12/2005 | Blin et al. |
| 2006/0104929 A1 | 5/2006 | Morita et al. |
| 2006/0120983 A1 | 6/2006 | Blin et al. |
| 2008/0254076 A1 | 10/2008 | Ferrari et al. |
| 2008/0292574 A1 | 11/2008 | Uehara |
| 2010/0303743 A1 | 12/2010 | Kennan et al. |
| 2011/0245374 A1 | 10/2011 | Barnes et al. |
| 2012/0156148 A1 * | 6/2012 | Shikano .................. A61K 8/891 424/59 |
| 2012/0220549 A1 | 8/2012 | Starch et al. |
| 2012/0251598 A1 | 10/2012 | Ikeda et al. |
| 2013/0064120 A1 | 3/2013 | Bodog et al. |
| 2014/0249106 A1 | 9/2014 | Starch et al. |
| 2015/0190516 A1 | 7/2015 | Cauvin et al. |
| 2017/0174885 A1 | 6/2017 | Fryfogle et al. |

FOREIGN PATENT DOCUMENTS

| | | |
|---|---|---|
| JP | 11001560 | 1/1999 |
| JP | 200181324 | 3/2001 |
| WO | 2004024117 | 3/2004 |
| WO | 2006045418 | 5/2006 |
| WO | 2006106362 | 10/2006 |
| WO | 2011028765 | 3/2011 |
| WO | 2011028770 | 3/2011 |
| WO | 2013117490 | 8/2013 |
| WO | 2014/019841 * | 2/2014 |
| WO | 2014019840 | 2/2014 |
| WO | 2014019841 | 2/2014 |
| WO | 2016164296 | 10/2016 |

# PITUITOUS SILICONE EMULSIONS

CROSS REFERENCE TO RELATED APPLICATIONS

This application is a U.S. national stage filing under 35 U.S.C. § 371 of PCT Application No. PCT/US16/025839 filed on 4 Apr. 2016, currently pending, which claims the benefit of U.S. Provisional Application No. 62/144,546 filed 8 Apr. 2015 under 35 U.S.C. § 119 (e). PCT Application No. PCT/US16/025839 and U.S. Provisional Application No. 62/144,546 are hereby incorporated by reference.

FIELD OF THE INVENTION

The present invention generally relates to emulsions comprising pituitous silicone fluids and to methods for preparing the emulsions. More specifically, this disclosure relates to emulsions comprising carrier fluids and pituitous silicone fluids that comprise a hydrosilylation reaction product of two linear organopolysiloxanes.

BACKGROUND

Silicone fluids are widely used in industry. The most common silicone fluids used are dimethylsiloxane fluids, which are typically low molecular weight cyclic molecules. However, high molecular weight and highly branched fluids are also used in many applications. The phenomenon of a viscoelastic liquid climbing a rotating rod, known as the Weissenberg effect, has been observed in polymer solutions, and in pituitous silicone fluids as described by Starch et al. (US2012/0220549 A1). This behavior is representative of entanglements between polymer chains that develop under shear stress. Pituitous silicone fluids are high molecular weight, highly branched organopolysiloxanes.

Pituitous silicone fluids are difficult to handle making their incorporation into formulations or emulsions difficult. Therefore, there remains a need for emulsions of pituitous silicone fluids and processes for making emulsions of pituitous silicone fluids that can make incorporation of pituitous silicone fluids into formulations easier.

SUMMARY OF THE INVENTION

The present invention provides methods for preparing emulsions of silicone fluids having pituitous rheological properties. The present invention also provides emulsions of silicone fluids having pituitous rheological properties and compositions comprising emulsions of silicone fluid having pituitous rheological properties.

In one embodiment, the present invention provides methods for preparing emulsions of a silicone fluid having pituitous rheological properties, the methods comprising: (A) forming an oil-in-water emulsion by: (i) combining a carrier fluid, a SiH-containing organopolysiloxane and an alkenyl-containing organpolyosiloxane to form a mixture, (ii) adding a surfactant to the mixture, and (iii) adding water and shearing to form an oil-in-water emulsion, wherein the mixture of the carrier, the SiH-containing organopolysiloxane and the alkenyl-containing organopolysiloxane forms an oil phase of the oil-in-water emulsion; and (B) reacting the SiH-containing organopolysiloxane and the alkenyl-containing organopolysiloxane in the oil phase of the emulsion formed in (A)(iii) in the presence of a hydrosilylation catalyst to form an emulsion of a silicone fluid having pituitous rheological properties.

DETAILED DESCRIPTION OF THE INVENTION

Figure 1:
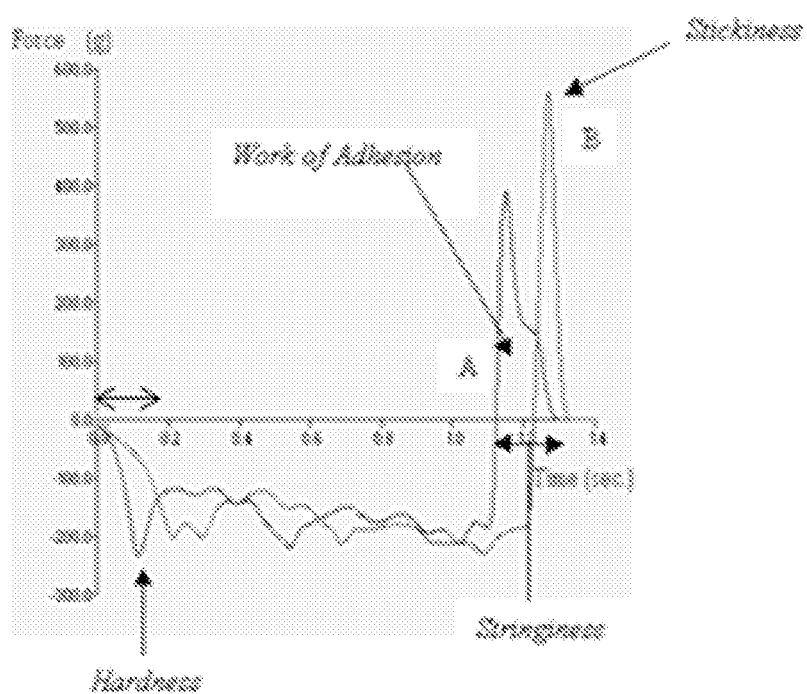
FIG. 1 shows the result of texture analysis for stickiness, stringiness and adhesion of a dried emulsion sample according to the invention.

The present invention provides emulsions of pituitous silicone fluids, that is, emulsions of silicone fluids that exhibits pituitous properties. As used herein, "pituitous" describes rheological properties of the silicone fluids wherein the fluids exhibit an increasing normal stress observed in a perpendicular direction when a constantly increasing shear force is applied. For example, when the pituitous fluid is subjected to shear stress in the x-y plane, a force is developed in the z direction (perpendicular or normal to the plane of shear). Pituitous rheological properties of the silicone fluid may be measured using a controlled stress rheometer. Such rheometers are commercially available, such as TA Instruments AR 1000-N (109 Lukens Drive, New Castle Del. 19720). Typically, a fluid sample is held between a flat disk (attached to the rheometer) and a stationary plate equipped with a load cell. A controlled amount of force (torque) is applied to the shaft attached to the disc, thus subjecting the sample to a shear stress. Typically, the torque is increased and the disc rotates at an increasing rate, which is recorded as the shear rate. As the sample is being subjected to the shear stress, the normal stress is recorded by the load cell. The results of the evaluations of the rheological properties are typically reported as a plot of normal stress in Pascals vs. a perpendicular shear rate in $sec^{-1}$.

In other embodiments, a fluid is considered pituitous if a plot of normal stress versus shear rate falls above a limit line on a graph wherein the limit line is created using the equation y=3.6x, where y in the normal stress and x is the shear rate. However, the results are not limited to such types of reporting and may be reported or evaluated using any technique appreciated in the art.

In various embodiments, the term "pituitous silicone fluid", as used herein, described a substance whose component particles can move past one another, that is flow, when a force is applied, such as gravity. In such embodiments, the fluid does not encompass gels, which do not flow. In other embodiments, the pituitous silicone fluid has a viscosity at 23° C. of at least 100 mPa·s (cP), alternatively of at least 200 mPa·s, or alternatively at least 300 mPa·s, each with a maximum of one of the values described above. In other embodiments, the pituitous silicone fluid has a viscosity at 23° C. from 100 to 10,000,000 mPa·s, alternatively from 100 to 1,000,000 mPa·s, alternatively from 100 to 100,000 mPa·s, alternatively from 100 to 50,000 mPa·s, alternatively from 100 to 10,000 mPa·s, alternatively from 200 to 10,000 mPa·s, alternatively from 200 to 50,000 mPa·s, alternatively form 300 to 10,000 mPa·s, alternatively from 300 to 50,000 mPa·s, alternatively from 100 to 40,000 mPa·s, alternatively from 100 to 30,000 mPa·s, alternatively from 100 to 20,000 mPa·s, alternatively from 100 to 9,000 mPa·s, alternatively from 100 to 8,000 mPa·s, alternatively from 100 to 7,000 mPa·s, alternatively from 100 to 6,000 mPa·s, alternatively from 100 to 5,000 mPa·s, alternatively from 100 to 4,000, alternatively from 100 to 3,000 mPa·s, alternatively from 100 to 2,000 mPa·s, or alternatively from 100 to 1,000 mPa·s.

Silicone having pituitous rheological properties may comprise branched organopolysiloxanes. In one embodiment, the branched organopolysiloxanes may be obtainable by the reaction of two linear organopolysiloxanes having hydrolyzable groups. For example, branched organopolysiloxanes having pituitous rheological properties may be prepared by condensation polymerization in a carrier fluid, wherein the condensation polymerization reaction product exhibits pituitous rheological properties.

In another embodiment, the branched organopolysiloxanes may be obtainable by a hydrosilylation reaction of two linear organopolysiloxanes in a carrier fluid, wherein the hydrosilylation reaction product exhibits pituitous rheological properties.

In one embodiment, the present invention provides emulsions comprising pituitous silicone fluids. In another embodiment, the present invention provides emulsions comprising pituitous silicone fluids comprising a hydrosilylation reaction product of two linear organopolysiloxanes, and including a carrier fluid, wherein the hydrosilylation reaction product exhibits pituitous rheological properties.

The term "substituted" as used in relation to another group, for example, a hydrocarbon group, means, unless indicated otherwise, one or more hydrogen atoms in the hydrocarbon group has been replaced with another substituent. Examples of such substituents include, for example, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic and carboxyl; nitrogen atoms; nitrogen atom containing groups such as amines, amino-functional groups, amido-functional groups, and cyano-functional groups; sulphur atoms; and sulphur atom containing groups such as mercapto groups.

For U.S. practice, all patent application publications and patents referenced herein, or a portion thereof if only the portion is referenced, are hereby incorporated herein by reference to the extent that incorporated subject matter does not conflict with the present description, which would control in any such conflict.

The term "alternatively" indicates a different and distinct embodiment.

The term "comprises" and its variants (comprising, comprised of) are open ended.

The term "consists of" and its variants (consisting of) are closed ended, and denotes the inclusion of only the materials or components or steps as recited except for impurities ordinarily associated therewith.

The term "consists essentially of" and its variants (consisting essentially of) are closed ended, and limits inclusion to the specified materials or components or steps and to those that do not materially affect the basic and characteristic (s) of the composition or method.

The term "may" confers a choice, not an imperative.

The articles 'a', 'an', and 'the' each refers to one or more, unless otherwise indicated by the context of the specification.

Unless indicated otherwise, alkyl, alkylaryl, aryl and alkenyl groups have the following definitions. An alkyl group means a moiety having 1 to 10 carbon atoms. An alkylaryl group means a moiety wherein the alkyl moiety has 1 to 10 carbon atoms and the aryl moiety has 6 to 20 carbon atoms. An aryl group means a moiety having 6 to 20 carbon atoms. An alkenyl group means a moiety having 2 to 10 carbon atoms.

In one embodiment, the present invention provides methods for preparing emulsions of a silicone fluid having pituitous rheological properties, the methods comprising: (A) forming an oil-in-water emulsion by: (i) combining a carrier fluid, a SiH-containing organopolysiloxane and an alkenyl-containing organpolyosiloxane to form a mixture, (ii) adding a surfactant to the mixture, and (iii) adding water and shearing to form an oil-in-water emulsion, wherein the mixture of the carrier, the SiH-containing organopolysiloxane and the alkenyl-containing organopolysiloxane forms an oil phase of the oil-in-water emulsion; and (B) reacting the SiH-containing organopolysiloxane and the alkenyl-containing organopolysiloxane in the oil phase of the emulsion formed in (A)(iii) in the presence of a hydrosilylation catalyst to form an emulsion of a silicone fluid having pituitous rheological properties. The silicone fluid having pituitous rheological properties comprises a hydrosilylation reaction product.

The Hydrosilylation Reaction Product

The hydrosilylation reaction product is the reaction product of a first linear organopolysiloxane and a second linear organopolysiloxane. That is, the hydrosilylation reaction product is formed from the hydrosilylation reaction of the first and second linear organopolysiloxanes. The hydrosilylation reaction product may itself be linear. In various embodiments, the terminology "linear" describes that the first linear organopolysiloxane, the second linear organopolysiloxane, the hydrosilylation reaction product, or the pituitous silicone fluid is not branched or not highly branched. By "not branched" or "not highly branched" is meant having less than 10, 1, 0.5, 0.1, or 0.01 weight percent of T and Q units, that is, siloxy units having the formulae ($R-SiO_{3/2}$) and ($SiO_{4/2}$), respectively.

In other embodiments, the terminology "linear" describes that the first linear organopolysiloxane, the second linear organopolysiloxane, the hydrosilylation reaction product, or the pituitous silicone fluid includes no branching or is not highly branched. The backbone of the first linear organopolysiloxane, the second linear organopolysiloxane, the hydrosilylation reaction product, or the pituitous silicone fluid is not branched or highly branched. For example, while the backbone of the first linear organopolysiloxane, the second linear organopolysiloxane, the hydrosilylation reaction product, or the pituitous silicone fluid is typically linear as defined above, the backbone may have one or more cyclic, aromatic, or otherwise non-linear substituents attached thereto. In such a scenario, the backbone would still be considered "linear" as used herein.

In some embodiments, one or more than one first linear organopolysiloxane may be reacted with one or more than one second linear organopolysiloxane. Similarly, in other embodiments, one first linear organopolysiloxane may be reacted with two or more second linear organopolysiloxanes. Alternatively, two first linear organopolysiloxanes may be reacted with one second linear organopolysiloxane. Thus, in various embodiments, wherever "first linear organopolysiloxane" is used, two or more first linear organopolysiloxanes may be used. In other embodiments, wherever "second linear organopolysiloxane" is used, two or more second linear organopolysiloxanes may be used. The hydrosilylation reaction product may include alkenyl or Si—H functionality, for example, unreacted functionalities from the reaction of the first and second linear organopolysiloxanes. In various embodiments, the alkenyl or Si—H functionality may be observed on a parts per million (ppm) or parts per billion (ppb) level, based on a total weight of the hydrosilylation reaction product and/or the pituitous silicone fluid. In other embodiments, the alkenyl or Si—H functionality is understood based on a molar ratio of alkenyl to Si—H functionality of the reactants, for example, the first and second linear organopolysiloxanes, used to form the reaction product. For example, the ratio of alkenyl to Si—H units used to form the hydrosilylation reaction product (for example, from the first and second linear organopolysiloxanes) may be less than 1 or greater than 1. In various embodiments, this ratio is from 0.01 to less than 1, from 0.1 to less than 1, from 0.2 to 0.9, from 0.3 to 0.8, from 0.4 to 0.7, or from 0.5 to 0.6. In other embodiments, this ratio is greater than 1, from greater than 1 to 100, from greater than 1 to 50, from greater than 1 to 25, from greater than 1 to 15, from greater than 1 to 10, or from greater than 1 to 5. It is contemplated that any and all values or ranges of values between those described above may also be utilized. Typically, the ratio of alkenyl to Si—H is not exactly 1. However, a ratio of 1 is contemplated in one embodiment.

The hydrosilylation reaction product may be present in the emulsion in an amount of from 25% to 95% by weight or 40% to 95% by weight. In various embodiments, the hydrosilylation reaction product may be present in an amount of from 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 40% to 85%, 40% to 80%, 40% to 75%, 40% to 70%, 40% to 65%, 40% to 60%, 40% to 55%, 40% to 50%, 40% to 45%, 50% to 95%, 55% to 95%, 60% to 95%, 65% to 95%, 70% to 95%, 75% to 95%, 80% to 95%, 85% to 95%, 90% to 95% by weight of the emulsion. This amount, may also be described as parts by weight, percent solids or percent active(s). It is contemplated that any and all values or ranges of values between those described above may also be utilized.

The hydrosilylation reaction product may be described as an elastomer, for example, a loosely cross-linked elastomer (medium to low crosslinking density). When combined with a carrier fluid, the hydrosilylation reaction product is substantially soluble therein, that is, at least 90% by weight of the hydrosilylation reaction product dissolves in the carrier fluid. The degree of polymerization of the hydrosilylation reaction product itself can depend on the degrees of polymerization of the first and second linear organopolysiloxanes, as described below. In various embodiments, a high degree of polymerization in both the first and second linear organopolysiloxanes imparts tight cross-linking (very high crosslinking density) to the hydrosilylation reaction product. In other embodiments, a high degree of polymerization in one or the other of the first and second linear organopolysiloxanes imparts a medium degree of cross-linking (medium to low crosslinking density) to the hydrosilylation reaction product. In still other embodiments, a low degree of polymerization of both the first and second linear organopolysiloxanes imparts low, for example, a loose, degree of cross-linking to the hydrosilylation reaction product.

In one embodiment of the present invention, the first linear organopolysiloxane comprises an alkenyl-containing organopolysiloxane, and the second linear organopolysiloxane comprises a SiH-containing organopolysiloxane.

The First Linear Organopolysiloxane

The first linear organopolysiloxane comprises ($R^1R^2R^3SiO_{1/2}$) and ($R^4R^5SiO_{2/2}$) units, also known as M and D units, respectively. Each of $R^1$ to $R^5$ is independently a hydrocarbon group provided that at least one of $R^1$ to $R^5$ is an alkenyl group (an alkenyl-containing organopolysiloxane). The hydrocarbon group may be an alkyl group having 1 to 20, 2 to 15, 3 to 10, 5 to 10, or 1 to 5 carbon atoms, such as, but not limited to, methyl, ethyl, propyl, butyl, pentyl and hexyl; cycloalkyl groups, such as, but not limited to, cyclohexyl and cycloheptyl; aryl groups having 6 to 12 carbon atoms, such as, but not limited to, phenyl, tolyl and xylyl; aralkyl groups having 7 to 20 carbon atoms, such as, but not limited to, benzyl and phenylethyl. The hydrocarbon group may also be an alkenyl group having 2 to 20 carbon atoms such as, but not limited to, vinyl, allyl, butenyl, pentenyl, hexenyl and decenyl, typically vinyl or hexenyl groups. Alternatively, the hydrocarbon group may include one or more halogen atoms. It is contemplated that any and all values or ranges of values between those described above may also be utilized.

In one embodiment, the alkenyl-containing organopolysiloxane is an organopolysiloxane having vinyl groups, wherein the vinyl groups may be pendant or terminal.

The first linear organopolysiloxane may be a homopolymer, a copolymer or a terpolymer. Non-limiting examples include copolymers including dimethylsiloxy units and phenylmethylsiloxy units, copolymers including dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. As described above, the first linear organopolysiloxane typically has a linear backbone but may include non-linear substituents attached to the backbone.

In various embodiments, the first linear organopolysiloxane includes less than 10, 1, 0.5, 0.1, or 0.01 weight percent of T and/or Q units. In another embodiment, the first linear organopolysiloxane is free of T and/or Q units. In still other embodiments, the first linear organopolysiloxane has a degree of polymerization of from 100 to 15,000. More typically, the degree of polymerization is from 100 to 10,000, from 500 to 10,000, from 2,000 to 15,000, from 5,000 to 15,000, from 7,500 to 15,000, from 10,000 to 15,000, from 8,000 to 12,000, or about 10,000. It is contemplated that any and all values or ranges of values between those described above may also be utilized.

In one embodiment, the first linear organopolysiloxane may be a polydiorganosiloxane gum. As used herein, polydiorganosiloxane gums include predominately D siloxy units. For example, the polydiorganosiloxane gum may itself have viscosity of at least 1,000,000 mm$^2$/s at 25° C., or alternatively 2,000,000 mm$^2$/s at 25° C. Alternatively, the molecular weight may be sufficient to impart a Williams plasticity number of at least 40 as determined by the American Society for Testing and Materials (ASTM) test method 926 to the gum. Typically, the plasticity number is 40 to 200, or alternatively 50 to 150. Alternatively, the molecular weight of the diorganopolysiloxane gum is at least 600,000 Daltons, or alternatively at least 1,000,000 Daltons, or alternatively at least 2,000,000 Daltons. It is contemplated that any and all values or ranges of values between those described above may also be utilized.

Specific non-limiting illustrations of polydiorganosiloxane gums include: trimethylsiloxy-endblocked dimethylsiloxane, trimethylsiloxy-endblocked dimethylsiloxane-methylvinylsiloxane copolymers; trimethylsiloxy-endblocked methylphenylsiloxane-dimethylsiloxane-methylvinylsiloxane copolymers; trimethylsiloxy-endblocked 3,3,3-trifluoropropylmethyl siloxane copolymers; trimethylsiloxy-endblocked 3,3,3-trifluoropropylmethyl-methylvinylsiloxane copolymers; dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers; and similar copolymers wherein at least one end group is dimethylhydroxysiloxy. The polydiorganosiloxane gum may also be or include a combination of two or more organopolysiloxanes. Methods for preparing polydiorganosiloxane gums are well known and many are commercially available.

In other embodiments, the first linear organopolysiloxane is a fluid. For example, the fluid may have a viscosity of from 1,000 to 100,000, from 25,000 to 100,000, from 25,000 to 75,000, from 50,000 to 100,000, from 50,000 to 75,000, from 50,000 to 60,000, or from 55,000 to 65,000, mm$^2$/s at 25° C. The fluid may alternatively have a molecular weight of from 7,500 to 700,000, from 50,000 to 500,000, or from 100,000 to 250,000, Daltons. In other embodiments, DOW CORNING fluids SFD 128, DC4-2764, DC2-7891, DC2-7754, DC2-7891, and DC2-7463, SFD-117, SFD-119, SFD 120, SFD 129, DC 5-8709, LV, 2-7038, DC 2-7892, 2-7287, 2-7463, dihexenyl terminal DC7692, DC7697, along with DC 2-7063 and DC 2-7748, and combinations thereof, may be used. It is contemplated that any and all values or ranges of values between those described above may also be utilized.

The Second Linear Organopolysiloxane

The second linear organopolysiloxane includes ($R^6R^7R^8SiO_{1/2}$) and ($R^9R^{10}SiO_{2/2}$) units, wherein each of $R^6$ to $R^{10}$ is independently a hydrocarbon group provided that at least one of $R^6$ to $R^{10}$ is a hydrogen atom (an SiH-containing organopolysiloxane). The hydrocarbon group may be any described above.

In various embodiments, the second linear organopolysiloxane includes less than 10, 1, 0.5, 0.1, or 0.01 weight percent of T and/or Q units. Alternatively, the second linear organopolysiloxane may be entirely free of T and/or Q units. In other embodiments, the second linear organopolysiloxane has a degree of polymerization of from 4 to 1000, from 8 to 500, from 25 to 400, from 50 to 300, from 75 to 200, from 75 to 100, from 100 to 500, from 100 to 400, from 100 to 300, from 100 to 200, from 75 to 150, from 75 to 125, or about 100. It is contemplated that any and all values or ranges of values between those described above may also be utilized.

The second linear organopolysiloxane may be a gum or a fluid, as described above. Non-limiting examples of the second linear organopolysiloxane are DC 5-0210, 6-3570, 1-8114, 1-3502, OFX-5057, OFX-5084, OFX-5625, MHX-1107, and combinations thereof. These are all commercially available products that represent SiH pendant, SiH terminal, or SiH homopolymers.

The Hydrosilylation Catalyst

The first and second linear organopolysiloxanes typically react together to form the hydrosilylation product. This reaction typically takes place in the presence of a hydrosilylation catalyst. This catalyst may be any known in the art. For example, the catalyst may be a platinum group metal-containing catalyst. By platinum group it is meant ruthenium, rhodium, palladium, osmium, iridium and platinum and complexes thereof. Non-limiting examples of platinum group metal-containing catalysts useful herein are the platinum complexes prepared as described in U.S. Pat. Nos. 3,419,593; 5,175,325; 3,989,668; 5,036,117; 3,159,601; 3,220,972; 3,296,291; 3,516,946; 3,814,730; and 3,928,629; each of which is expressly incorporated herein by reference in one or more non-limiting embodiments. The platinum-containing catalyst can be platinum metal, platinum metal deposited on a carrier such as silica gel or powdered charcoal, or a compound or complex of a platinum group metal. Typical platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. Pat. No. 6,605,734, which is expressly incorporated herein by reference in one or more non-limiting embodiments.

The amount of catalyst used typically depends upon the particular catalyst. The catalyst is typically utilized in an amount sufficient to provide at least 2 parts per million (ppm), typically 4 to 200 ppm of platinum based on total weight percent solids (all non-solvent ingredients), based on one million parts of the pituitous silicone fluid. In various embodiments, the catalyst is present in an amount sufficient to provide 1 to 150 weight ppm of platinum on the same basis. The catalyst may be added as a single species or as a mixture of two or more different species.

The molar ratio of the alkenyl functional group to the SiH functional group (alkenyl:SiH molar ratio) may be from 0.01 to 10, 0.05 to 10, 0.1 to 10, 0.5 to 10, 1.0 to 10, 3 to 10, 5 to 10, 7 to 10, 0.01 to 7, 0.01 to 5, 0.01 to 3, 0.01 to 1, 0.05 to 1, 0.1 to 1, 0.05 to 7, 0.1 to 5, or 1 to 3. The first linear organopolysiloxane may comprise from 2 to 10 alkenyl groups per molecule, or from 2 to 7 alkenyl groups per molecule, or from 2 to 5 alkenyl groups per molecule. The second linear organopolysiloxane may comprise from 2 to 10 SiH groups per molecule, or from 2 to 7 SiH groups per molecule, or from 2 to 5 SiH groups per molecule.

Optional Compound

The emulsions of the present invention may comprise pituitous silicone fluid and one or more optional compounds. Alternatively, the pituitous silicone fluid comprising a hydrosilylation reaction product may be further defined as the reaction product of the first linear organopolysiloxane, the second linear organopolysiloxane, and one or more optional compounds in the presence of the aforementioned catalyst. Alternatively, the first linear organopolysiloxane may be reacted with the optional compound before or after reaction with the second linear organopolysiloxane. In other embodiments, the second linear organopolysiloxane may be reacted with the optional compound before reaction with the first linear organopolysiloxane and still fall within the general description of the second linear organopolysiloxane described above. For example, in one embodiment, a first type of second linear organopolysiloxane may be reacted with the optional compound to form a second type of second linear organopolysiloxane. Alternatively, this first type of second linear organopolysiloxane may be described as a species of the broad second linear organopolysiloxane. In one embodiment, the second linear organopolysiloxane includes the reaction product of a first species of the second linear organopolysiloxane and a compound having a mono terminal aliphatic unsaturated hydrocarbon group or any other optional compound described herein.

Non-limiting examples of such optional compounds include a compound or mixture of compounds having a mono terminal aliphatic unsaturated hydrocarbon group. For example, this optional compound may be or include a hydrocarbon containing 2-30 carbon atoms having one terminal unsaturated aliphatic hydrocarbon group, and/or a polyoxyalkylene having one terminal unsaturated aliphatic group.

Use of an optional compound may alter the resulting chemical and physical properties of the hydrosilylation reaction product and/or the emulsions of the pituitous silicone fluid. For example, the optional compound may add hydrocarbon groups to the hydrosilylation reaction product, thus adding more hydrophobic character to the pituitous silicone fluid. Conversely, if the optional compound is, for example, a polyoxyalkylene having a majority of ethylene oxide units, its use may result in increase hydrophilicity of the hydrosilylation reaction product and/or the pituitous silicone fluid. The optional compound may also have other functionalities, for example, amino and/or hydroxy.

The unsaturated aliphatic hydrocarbon group(s) in the optional compound can be an alkenyl or alkynyl group. Representative, non-limiting examples of the alkenyl groups are shown by the following structures: $H_2C=CH-$, $H_2C=CHCH_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures: $HC\equiv C-$, $HC\equiv CCH_2-$, $HC\equiv CC(CH_3)-$, $HC\equiv CC(CH_3)_2-$, and $HC\equiv CC(CH_3)_2CH_2-$.

In other embodiments, the hydrocarbon containing 2-30 carbons having one terminal unsaturated aliphatic group may be selected from alpha olefins such as 1-hexene, 1-octene, 1-decene, 1-undecene, 1-decadecene, and homologs. Alternatively, the optional compound may also be selected from aryl containing hydrocarbons such as alpha methyl styrene. Still further, the optional compound may be selected from those polyoxyalkylenes having the average formula $R'O-[(C_2H_4O)c'(C_3H_6O)d'(C_4H_8O)e]-R''$ where R' is a monovalent unsaturated aliphatic hydrocarbon group containing 2 to 12 carbon atoms, c' is from 0 to 100, d' is from 0 to 100, e is from 0 to 100, providing the sum of c', d', and e is >0, R'' is hydrogen, an acyl group, or a monovalent hydrocarbon group containing 1 to 8 carbons.

Representative, non-limiting examples of polyoxyalkylenes, useful as the optional compound include $H_2C=CHCH_2O(C_2H_4O)c'H$; $H_2C=CHCH_2O(C_2H_4O)c'CH_3$; $H_2C=CHCH_2O(C_2H_4O)c'C(O)CH_3$; $H_2C=CHCH_2O(C_2H_4O)c'(C_3H_6O)d'H$; $H_2C=CHCH_2O(C_2H_4O)c'(C_3H_6O)d'CH_3$; $H_2C=C(CH_3)CH_2O(C_2H_4O)c'H$; $H_2C=CC(CH_3)_2O(C_2H_4O)c'H$; $H_2C=C(CH_3)CH_2O(C_2H_4O)c'CH_3$; $H_2C=C(CH_3)CH_2O(C_2H_4O)c'C(O)CH_3$; $H_2C=C(CH_3)CH_2O(C_2H_4O)c'(C_3H_6O)d'H$; $H_2C=C(CH_3)CH_2O(C_2H_4O)c'(C_3H_6O)d'CH_3$; $HC\equiv CCH_2O(C_2H_4O)c'H$; $HC\equiv CCH_2O(C_2H_4O)c'CH_3$; $HC\equiv CCH_2O(C_2H_4O)c'C(O)CH_3$; $HC\equiv CCH_2O(C_2H_4O)c'(C_3H_6O)d'H$; $HC\equiv CCH_2O(C_2H_4O)c'(C_3H_6O)d'CH_3$; $HC\equiv CCH_2O(C_2H_4O)c'C(O)CH_3$; wherein c' and d' are as described above.

In still another embodiment, the optional compound may be a linear or branched siloxane with one unsaturated aliphatic group. Alternatively, the optional compound may be a polyol having one unsaturated aliphatic group, for example, allyl xylitol or allyl glycerin. Branched siloxane or organopolysiloxane means a siloxane or organopolysiloxane having greater than 10 weight percent of T and/or Q units.

The emulsion of a silicone fluid having pituitous rheological properties may further comprise a silicone resin and/or silicone elastomer. The silicone resins may be an MQ resin. The silicone resins may be resins having T and/or Q units. Resins having Q units comprise (1) one or more Q units of the formula ($SiO_{4/2}$); (2) from 15 to 995 D units of the formula $R^b_2SiO_{2/2}$ which units (1) and (2) may be inter-linked in any appropriate combination; and (3) M units of the formula $R^aR^b_2SiO_{1/2}$, wherein each $R^a$ substituent is selected from the group consisting of an alkyl group having from 1 to 6 carbon atoms, an alkenyl group having from 1 to 6 carbon atoms and an alkynyl group having from 1 to 6 carbon atoms, at least three $R^a$ substituents in the branched siloxane being alkenyl or alkynyl units, and each $R^b$ substituent is selected from the group consisting of an alkyl group having from 1 to 6 carbon atoms, an alkenyl group having 2 to 6 carbon atoms, an aryl group, an alkoxy group, an acrylate group and a methacrylate group.

The resin having Q units may be prepared by equilibrating a) tetrakis(vinyldimethylsiloxy)silane, and b) dimethyl cyclic siloxanes wherein the weight ratio of b:a is at least 99:1

The Carrier Fluid

The emulsions of pituitous silicone fluid includes a carrier fluid chosen from a silicone fluid, an organic solvent, an organic oil, and any combination thereof. The carrier fluid may be referred to as a solvent. Suitable carrier fluids include silicones, both linear and cyclic, organic oils, organic solvents and combinations of these. Specific examples of solvents may be found in U.S. Pat. No. 6,200,581, which is hereby expressly incorporated by reference in various non-limiting embodiments relative to these solvents.

In one embodiment, the carrier fluid is polydimethylsiloxane. In various other embodiments, the carrier fluid is a low viscosity silicone or a volatile methyl siloxane or a volatile ethyl siloxane or a volatile methyl ethyl siloxane having a viscosity from 1 to 1,000 mm$^2$/sec measured at 25° C., such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadecamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, and and combination thereof. Referring back to the organic solvents, the organic solvent may include, but are not limited to, aromatic hydrocarbons, aliphatic hydrocarbons, alcohols, aldehydes, ketones, amines, esters, ethers, glycols, glycol ethers, alkyl halides, aromatic halides, and combinations thereof. Hydrocarbons including isododecane, isohexadecane, Isopar L ($C_{11}$-$C_{13}$), Isopar H ($C_{11}$-$C_{12}$), hydrogenated polydecene, and combinations thereof may also be used. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, octyl palmitate, and combinations thereof may also be used. Organic fats, oils, fatty acids, fatty alcohols, and combinations thereof, may also be used.

The carrier fluid typically has a viscosity of from 1 to 1,000, from 2 to 50, from 5 to 50, from 2 to 5, from 2 to 10, from 2 to 15, from 2 to 20, mm$^2$/sec measured at 25° C. The carrier fluid is typically present in the emulsions of the pituitous silicone fluid in an amount from 1% to 90%, 1% to 85%, 1% to 80%, 5% to 90, 5% to 85%, 5% to 80%, 10% to 90%, 10% to 85%, 10% to 80%, 10% to 75%, 15% to 90%, 15% to 85%, 15% to 80%, 15% to 75%, 15% to 70%, 15% to 65%, 20% to 65%, 30% to 65%, or 30% to 55% by weight of the emulsion of pituitous silicone fluid. It is contemplated that any and all values or ranges of values between those described above may also be utilized.

The combination of the carrier fluid and the hydrosilylation reaction product provide emulsions of the pituitous silicone fluid with a viscosity, measured in Pascal seconds (Pa·s) and collected relative to the shear rate in sec$^{-1}$. In one embodiment, the viscosity is 7,000 mPa·s (cP). In another embodiment, the viscosity is from 1 to 100,000 mPa·s, 1 to 75,000 mPa·s, 1 to 50,000 mPa·s, 1 to 25,000 mPa·s, 1 to 10,000 mPa·s, 1 to 7,000 mPa·s, from 100 to 7,000 mPa·s, from 500 to 7,000 mPa·s, from 1,000 to 7,000 mPa·s, from 2,000 to 7,000 mPa·s, from 3,000 to 7,000 mPa·s, from 4,000 to 7,000 mPa·s, from 5,000 to 7,000 mPa·s, from 6,000 to 7,000 mPa·s, 1 to 6,000 mPa·s, 1 to 5,000 mPa·s, 1 to 4,000 mPa·s, 1 to 3,000 mPa·s, 1 to 2,000 mPa·s, 1 to 1,000 mPa·s, 1 to 500 mPa·s, or 1 to 500 mPa·s. These viscosity values are typically measured using a Brookfield Viscometer RVDVII, spindle 4, 20 rpm. It is contemplated that any and all values or ranges of values between those described above may also be utilized.

The Emulsion

As used herein, and unless indicated otherwise, "emulsion" describes a water continuous emulsions (for example, an oil in water emulsion, or a silicone fluid in water emulsion), oil or silicone continuous emulsions (water in oil emulsions or water in silicone fluid emulsions), or multiple emulsions (water/oil/water, oil/water/oil types, water/silicone/water, or silicone/water/silicone). The emulsions of pituitous silicone fluid may be prepared using any techniques of the art such as stirring, homogenizing, and sonalating, for example, a batch, semi-continuous, or continuous process.

In one embodiment, the emulsion is an oil-in-water emulsion and may include at least one surfactant. The surfactant may vary, but typically is chosen from those surfactants that enhance the formation of water continuous emulsions. The surfactant may be an anionic surfactant, cationic surfactant, nonionic surfactant, amphoteric surfactant, or a mixture of any of these surfactants.

The surfactant may be in an amount from 0.01% to 20%, from 0.01% to 15%, from 0.01% to 10%, from 0.1% to 20%, from 0.1% to 15%, from 0.1% to 10%, from 0.5% to 10%, or from 0.5% to 5% by weight of the emulsion.

Examples of anionic surfactants include, but are not limited to, alkali metal, amine, or ammonium salts of higher fatty acids, alkylaryl sulphonates such as sodium dodecyl benzene sulfonate, long chain fatty alcohol sulfates, olefin sulfates and olefin sulfonates, sulfated monoglycerides, sulfated esters, sulfonated ethoxylated alcohols, sulfosuccinates, alkane sulfonates, phosphate esters, alkyl isethionates, alkyl taurates, alkyl sarcosinates, and mixtures thereof.

Examples of cationic surfactants include, but are not limited to, alkylamine salts, quaternary ammonium salts, sulphonium salts, and phosphonium salts.

Examples of amphoteric surfactants include, but are not limited to, imidazoline compounds, alkylaminoacid salts, betaines, and mixtures thereof.

Examples of suitable nonionic surfactants include, but are not limited to, condensates of ethylene oxide with long chain fatty alcohols or fatty acids such as a C12-16 alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, and mixtures thereof. Further examples of nonionic surfactants include polyoxyethylene fatty alcohols such as polyoxyethylene (23) lauryl ether, polyoxyethylene (4) lauryl ether; ethoxylated alcohols such as ethoxylated trimethylnonanol, $C_{12}$-$C_{14}$ secondary alcohol ethoxylates, ethoxylated, C10-Guerbet alcohol, ethoxylated, iso-C13 alcohol; poly(oxyethylene)-poly(oxypropylene)-poly(oxyethylene) tri-block copolymer (also referred to as poloxamers); tetrafunctional poly(oxyethylene)-poly(oxypropylene) block copolymer derived from the sequential addition of propylene oxide and ethylene oxide to ethylene diamine (also referred to as poloxamines), silicone polyethers, polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants, and combinations thereof.

When mixtures containing nonionic surfactants are used, one nonionic surfactant may have a low Hydrophile-Lipophile Balance (HLB) and the other nonionic surfactant(s) may have a high HLB, such that the nonionic surfactants have a combined HLB of 11-15, alternatively a combined HLB of 12.5-14.5.

Further examples of nonionic surfactants include polyoxyethylene alkyl ethers, polyoxyethylene alkylphenol ethers, polyoxyethylene lauryl ethers, straight-chain, primary alcohol alkoxylates, straight-chain secondary alcohol alkoxylates, alkyl phenol alkoxylates, olefinic alkoxylates, branched chain alkoxylates, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Further examples of nonionic surfactants include dimethicone copolyols, fatty acid esters of polyols, for instance sorbitol or glyceryl mono-, di-, tri- or sesquioleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Further examples of anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Further examples of amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

The emulsions of the present invention may be selected from those considered in the art to be a "macro" or "micro" emulsion. In other words, the average particle size of the emulsions may vary from 0.001 to 1000 μm, alternatively from 0.01 to 20 μm, or alternatively from 0.02 to 10 μm. The emulsions may be a microemulsion having an average particle size of less than 100 nm.

Particle size may be measured by a Malvern-Mastersizer® 2000 or a Microtrac-Nanotrac®. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv, as used herein, represents the average volume particle size of the dispersed particles. Dv 50 (or Dv0.5) is the particle size measured in volume corresponding to 50% of the cumulative particle population. In other words, if Dv 50=10 μm, 50% of the particle have an average volume particle size below 10 μm and 50% of the particle have a volume average particle size above 10 μm. Dv 90 (or Dv0.9) is the particle size measured in volume corresponding to 90% of the cumulative particle population, and Dv 10 (or Dv0.1) is the particle size measured in volume corresponding to 10% of the cumulative particle population.

The preparing the emulsions of the present invention involves adding water and mixing. Mixing may be shear mixing. Mixing can be accomplished by any method known in the art to effect mixing. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch equipments with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments. Alternatively, mixing may also occur via those techniques known in the art to provide high shear mixing to effect formation of emulsions. Representative of such high shear mixing techniques include high speed stirrers, homogenizers, Sonolators®, Microfluidizers®, Ross mixers, Eppenbach colloid mills, Flacktek Speedmixers®, and other similar shear devices.

The temperature and pressure at which the mixing occurs is not critical, but generally is conducted at ambient temperature and pressures. Typically, the temperature of the mixture will increase during the mixing process due to the mechanical energy associated when shearing high viscosity materials.

The amount of the added water may vary. Typically the amount of added water may vary from 1 to 1000 parts by weight of the mixture, alternatively from 5 to 500 parts per 100 parts by weight, or alternatively from 5 to 100 parts per 100 parts by weight.

The water is added to the mixture at such a rate with mixing so as to form an emulsion. The water added to the mixture may be done in incremental portions, whereby each incremental portion comprises less than 50 weight % of the mixture, alternatively 25 weight % of the mixture, and each incremental portion of water is added successively to the previous after the dispersion of the previous incremental portion of water, wherein sufficient incremental portions of water are added to form the emulsion.

In one embodiment, the emulsion produced according to the present invention may contain less than 1.0 weight % cyclosiloxanes, alternatively contains less than 0.5 weight % cyclosiloxanes, alternatively contains less than 0.1 weight % cyclosiloxanes. In another embodiment, the emulsion may contain less than 1.0 weight % of each octamethylcyclotetrasiloxanes ($D_4$) and decamethylcyclopentasiloxanes ($D_5$), alternatively contains less than 0.5 weight % of each octamethylcyclotetrasiloxanes ($D_4$) and decamethylcyclopentasiloxanes ($D_5$), or alternatively contains less than 0.1 weight % of each octamethylcyclotetrasiloxanes ($D_4$) and decamethylcyclopentasiloxanes ($D_5$). The low amounts of cyclosiloxanes is achieved by removing the cyclosiloxanes, or without having to perform additional steps for removing cyclosiloxanes.

The emulsions of the present invention may contain additional components. The additional components may be one or more of the optional compound described above. The additional components may include solvents, diluents, or mixtures thereof. Solvents include low molecular weight organic solvents that are highly soluble in water, for example, C1-C4 monohydric alcohols, C2-C5 polyhydric alcohols including alkylene glycols, polyalkylene glycols, alkylene carbonates, and mixtures thereof. Typical solvents include ethanol, propanol, isopropanol, n-butyl alcohol, t-butyl alcohol, ethylene glycol, diethylene glycol, propylene glycol, dipropylene glycol, glycerol, propylene carbonate, and mixtures thereof. Further additional components may include, but are not limited to, color treatments, thickeners, water phase stabilizing agents, pH controlling agents, preservatives and biocides, pigments, colorants, dyes, soil release agents, oxidizing agents, reducing agents, inorganic salts, antibacterial agents, antifungal agents, bleaching agents, sequestering agents, and mixtures thereof.

The emulsions of the present invention are useful for making personal care compositions and compositions for hair shampoo, hair conditioner, hair treatment, and skin care. The emulsions of the the present invention are also useful in antifoam compositions and for providing softening benefits to fabric.

The Personal Care Composition

The invention also provides personal care compositions, which may also be described as personal care products or compositions. The personal care compositions include the emulsions of the pituitous silicone fluid described above. The personal care compositions may be in the form of a cream, a gel, a powder, a paste, or a freely pourable liquid. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care compositions may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care compositions may be formulated with a carrier that permits application in any conventional form, including but not limited to, liquids, rinses, lotions, creams, pastes, gels, foams, mousses, ointments, sprays, aerosols, soaps, sticks, soft solids, solid gels, and gels. Suitable carriers are appreciated in the art.

The personal care composition can be used in or for a variety of personal, household, and healthcare applications. In particular, the emulsions of the pituitous silicone fluid and/or personal care compositions of the present disclosure may be used in the personal care products as described in U.S. Pat. Nos. 6,051,216; 5,919,441; and 5,981,680; WO 2004/060271 and WO 2004/060101; in sunscreen compositions as described in WO 2004/060276; in cosmetic compositions also containing film-forming resins, as described in WO 03/105801; in the cosmetic compositions as described in US Pat. App. Pub. Nos. 2003/0235553; 2003/0072730 and 2003/0170188, in EP Pat. Nos. 1,266,647; 1,266,648 and 1,266,653, in WO 03/105789, WO 2004/000247 and WO 03/106614; as additional agents to those described in WO 2004/054523; in long wearing cosmetic compositions as described in US Pat. App. Pub. No. 2004/0180032; and/or in transparent or translucent care and/or make up compositions as described in WO 2004/054524, all of which are expressly incorporated herein by reference in various non-limiting embodiments.

The personal care composition and/or emulsions of the pituitous silicone fluid can be used by standard methods, such as applying them to the human body, for example, skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care composition and/or emulsions of the pituitous silicone fluid may be used in a conventional manner for example for conditioning the skin. An effective amount of the personal care composition and/or pituitous silicone fluid may be applied to the skin. Such effective amounts generally be from 1 mg/cm$^2$ to 3 mg/cm$^2$. Application to the skin typically includes working the personal care composition and/or emulsions of the pituitous silicone fluid into the skin. This method for applying to the skin typically includes the steps of contacting the skin with the personal care composition and/or emulsions of the pituitous silicone fluid in an effective amount and then rubbing the personal care composition and/or emulsions of the pituitous silicone fluid into the skin. These steps can be repeated as many times as desired to achieve the desired benefit.

Use of the personal care compositions and/or emulsions of the pituitous silicone fluid on hair may use a conventional manner for conditioning hair. An effective amount of the personal care composition and/or emulsions of the pituitous silicone fluid for conditioning hair is applied to the hair. Such effective amounts generally be from 1 g to 50 g, typically from 1 g to 20 g. Application to the hair typically includes working the personal care composition and/or pituitous silicone fluid through the hair such that most or all of the hair is contacted with the personal care composition and/or emulsions of the pituitous silicone fluid. This method for conditioning the hair typically includes the steps of applying an effective amount of the personal care composition and/or emulsions of the pituitous silicone fluid to the hair, and then working the personal care composition and/or pituitous silicone fluid through the hair. These steps can be repeated as many times as desired to achieve the desired conditioning benefit.

Non-limiting examples of additives which may be formulated into the personal care composition and/or emulsions of the pituitous silicone fluid include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-carie and wound healing-promotion agents.

The personal care composition, such as a shampoo or cleanser, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the shampoo composition in an amount from 5 to 50 wt % and typically 5 to 25 wt % based on the total weight of the shampoo composition.

The personal care composition may include at least one cationic deposition aid, typically a cationic deposition polymer. The cationic deposition aid is typically present at levels of from 0.001 to 5%, typically from 0.01 to 1%, more typically from 0.02% to 0.5% by weight. The cationic deposition polymer may be a homopolymer or be formed from two or more types of monomers. The molecular weight of the cationic deposition polymer is typically from 5,000 to 10,000,000, typically at least 10,000 and typically from 100,000 to 2,000,000. The cationic deposition polymers typically have cationic nitrogen containing groups such as quaternary ammonium or protonated amino groups, or a combination thereof. The cationic charge density has been found to need to be at least 0.1 meq/g, typically above 0.8 or higher. The cationic charge density should not exceed 4 meq/g, it is typically less than 3 and more typically less than 2 meq/g. The charge density can be measured using the Kjeldahl method and is within the above limits at the desired pH of use, which will in general be from 3 to 9 and typically from 4 to 8. It is contemplated that any and all values or ranges of values between those described above may also be utilized. The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers typically have C1-C7 alkyl groups, more typically C1-C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g. alkyl vinyl imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls such as the C1-C7 alkyls, more typically C1 and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically C1-C 7 hydrocarbyls, more typically C1-C3, alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquaternium-16) such as those commercially available from BASF Wyandotte Corp. (Parsippany, N.J., USA) under the LUVIQUAT tradename (e.g. LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g. GAFQUAT 755N); cationic diallyl quaternary ammonium-containing polymer including, for example, dimethyl diallyammonium chloride homopolymer and copolymers of acrylamide and dimethyl diallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments.

Other cationic deposition aids that can be used include polysaccharide polymers, such as cationic cellulose derivatives and cationic starch derivatives. Cationic polysaccharide polymer materials suitable for use in compositions of the disclosure include those of the formula: A-O(R—N$^+$R$^1$R$^2$R$^3$X$^-$) wherein A is an anhydroglucose residual group, such as starch or cellulose anhydroglucose residual, R is an alkylene oxyalklene, polyoxyalkylene, or hydroxyalkylene group, or combination thereof, R$^1$, R$^2$ and R$^3$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^1$, $R^2$, $R^3$) typically being 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide.

Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the shampoo compositions in an amount from 1 to 15 wt % and more typically 2 to 10 wt % based on the total weight of the composition. The composition may further include a polyalkylene glycol to improve lather performance. Concentration of the polyalkylene glycol in the shampoo composition may be from 0.01% to 5%, typically from 0.05% to 3%, and more typically from 0.1% to 2%, by weight of the shampoo composition. The optional polyalkylene glycols are characterized by the general formula: $H(OCH_2CHR)_n$—OH wherein R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from 1500 to 25,000, typically from 2500 to 20,000, and more typically from 3500 to 15,000. Polyethylene glycol polymers useful herein are PEG-2M wherein R equals H and n has an average value of 2,000 (PEG-2M is also known as Polyox WSR9N-10, which is available from Union Carbide and as PEG-2,000); PEG-5M wherein R equals H and n has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of 7,000 (PEG-7M is also known as Polyox WSRO N-750 available from Union Carbide); PEG-9M wherein R equals H and n has an average value of 9,000 (PEG 9-M is also known as Polyox WSRS N-3333 available from Union Carbide); and PEG-14 M wherein R equals H and n has an average value of 14,000 (PEG-14M is also known as Polyox WSRO N-3000 available from Union Carbide). Other useful polymers include the polypropylene glycols and mixed polyethylene/polypropylene glycols.

The personal care composition may include a suspending agent at concentrations effective for suspending a silicone conditioning agent, or other water-insoluble material, in dispersed form in the personal care composition. Such concentrations may be from 0.1% to 10%, typically from 0.3% to 5.0%, by weight of the personal care composition. Suspending agents include crystalline suspending agents which can be categorized as acyl derivatives, long chain amine oxides, and combinations thereof, concentrations of which can be from 0.1% to 5.0%, typically from 0.5% to 3.0%, by weight of the shampoo compositions. These suspending agents are described in U.S. Pat. No. 4,741,855, which is expressly incorporated herein by reference in one or more non-limiting embodiments. These typical suspending agents include ethylene glycol esters of fatty acids typically having from 16 to 22 carbon atoms. More typical are the ethylene glycol stearates, both mono and distearate, but particularly the distearate containing less than 7% of the mono stearate.

Other suitable suspending agents include alkanol amides of fatty acids, typically having from 16 to 22 carbon atoms, more typically 16 to 18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g. Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g. stearyl dimethyl amine oxide. Other suitable suspending agents include xanthan gum at concentrations ranging from 0.3% to 3%, typically from 0.4% to 1.2%, by weight of the shampoo compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the shampoo compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid crosslinked with polyallylsucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care compositions may include one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care compositions may include one or more oils independent from the carrier fluid described above. The term "oil" as used herein describes any material which is substantially insoluble in water. Suitable oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate and silicones especially cyclomethicone and dimethicone and combinations thereof. Suitable low viscosity oils have a viscosity of 5 to 100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity surface oils generally have a viscosity of 200-1,000,000 mPas at 25° C., typically a viscosity of 100,000-250,000 mPas. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is 1:15 to 15:1, typically 1:10 to 10:1 respectively. The typical formulation of the disclosure includes 1 to 20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojaba, olive or cereal germ oil, may be utilized. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care compositions may include various waxes. The waxes generally have a melting point of from 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care compositions may include a powder. The powder may be generally defined as dry, particulate matter having a particle size of 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature.

The powder may also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent colouring agent, such as carbon black, chromium or iron oxides, ultramarines, manganese pyrophosphate, iron blue, and titanium dioxide, pearlescent agents, generally used as a combination with coloured pigments, or some organic dyes, generally used as a combination with coloured pigments and commonly used in the cosmetics industry, can be added to the composition. In general, these colouring agents can be present in an amount by weight from 0 to 20% with respect to the weight of the personal care composition. The powder may comprise a silicone powder. Silicone powders are compositions having a organopolysiloxane in powder form, that is, in which water or liquid or solvent has been removed. The silicone powder can be prepared from an emulsion of a silicone (organopolysiloxane) by removing the water or any solvent. The silicone or organopolysiloxane can be a silicone elastomer, a silicone resin, a silicone gum or a silicone fluid.

Pulverulent inorganic or organic fillers can also be added, generally in an amount by weight from 0 to 40% with respect to the weight of the personal care composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked. The fillers may typically be present in a proportion of from 0 to 35% of the total weight of the composition, more typically 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap and silicone resin microbeads (TOSPEARL from Toshiba, for example).

The personal care compositions may include a sunscreen. Sunscreens typically absorb ultraviolet light between 290-320 nanometers (the UV-B region) such as, but not exclusively, para-aminobenzoic acid derivatives and cinnamates such as octyl methoxycinnamate and those which absorb ultraviolet light in the range of 320-400 nanometers (the UV-A region) such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-di-methylaminobenzoate. In various embodiments, the sunscreen is as described in EP-A-678,292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one SO3 H group, mention may be made more particularly of 3-benzylidine-2-camphorsulphonic derivatives. A particularly typical compound is benzene-1, 4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl) benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy) benzylidenecamphor-10-sulphonic acid, 3-(4-methoxy) benzylidenecamphor-10-sulphonic acid, 3-(4,5-dimethoxy) benzylidenecamphor-10-sulphonic acid, 3-(4-n-butoxy) benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, and FR 2,236,515, 2,282,426, 2,645,148, 2,430, 938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the disclosure in a content which can be from 0.1 to 20%, typically from 0.2 to 10%, by weight relative to the total weight of the personal care composition.

Additional lipophilic screening agents can be utilized such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in the disclosure, mention may also be made of p-methylbenzylidenecamphor, which is also known as a UV-B absorber and is sold in particular under the trade name "Eusolex 6300" by Merck. The lipophilic screening agent(s) can be present in the composition according to the disclosure in a content which can be from 0.5 to 30%, typically from 0.5 to 20%, of the total weight of the composition. Other examples of lipophilic or hydrophilic organic screening agents are described in patent application EP-A-0,487,404, which is expressly incorporated herein by reference in one or more non-limiting embodiments. The cosmetic and/or dermatological compositions according to the disclosure can also include pigments or alternatively nanopigments (average primary particle size: generally between 5 nm and 100 nm, typically between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminium stearate, and silicones. Such coated or uncoated metal oxide nanopigments are described in particular in patent applications EP-A-0,518,772 and EP-A-0,518,773, each of which is expressly incorporated herein by reference in one or more non-limiting embodiments.

A thickening agent may be utilized in the personal care composition to provide a convenient viscosity. For example, viscosities of from 500 to 25,000 mm$^2$/s at 25° C. or more alternatively of from 3,000 to 7,000 mm$^2$/s at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or combinations of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in a shampoo composition, may provide a viscosity of from 500 to 25,000 mm$^2$/s at 25° C. Alternatively the thickening agent may be present in an amount from 0.05 to 10 wt % and alternatively 0.05 to 5 wt % based on the total weight of the personal care composition.

Stabilizing agents can also be used, e.g. in a water phase of an emulsion. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1 to 5 wt % and more alternatively 0.5 to 3 wt % of the personal care composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Referring back, the emulsion can be used in anti-perspirant and deodorant compositions under but not limited to the form of sticks, soft solid, roll on, aerosol, and pumpsprays. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care compositions can be an aerosol in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions, other than the present emulsions of the pituitous silicone fluid and the carrier fluid, may also be included in the personal care compositions. For example, such silicones include silicone fluids, gums, resins, elastomers; silicone surfactants and emulsifiers such as silicone polyethers, organofunctional silicones such as amino functional silicones and alkylmethylsiloxanes. Alkylmethylsiloxanes may be included in the present compositions. These siloxane polymers generally typically have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkylmethysiloxanes can be used in the composition.

Silicone gums other than those described above may also be included in the personal care compositions. Suitable non-limiting gums include insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C. up to 20 million centistoke (mm$^2$/s) at 25° C. Compositions of this type in are described for example in U.S. Pat. No. 6,013,682, which is expressly incorporated herein by reference in one or more non-limiting embodiments.

Silicone resins may also be included in the personal care composition. These resins are generally highly crosslinked polymeric siloxanes. Crosslinking is typically obtained by incorporating trifunctional and/or tetrafunctional silanes with the monofunctional silane and/or difunctional silane monomers used during manufacture. The degree of crosslinking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be used. Commercially available silicone resins suitable for applications herein are generally supplied in an unhardened form in low viscosity, volatile or nonvolatile silicone fluids. The silicone resins may be incorporated into compositions of the disclosure in their non-hardened forms rather than as hardened resinous structures.

Silicone carbinol fluids may be included in the personal care composition. These materials can be commonly described as substituted hydrocarbyl functional siloxane fluids or resins and some are described in WO 03/101412 A2, which is expressly incorporated herein by reference in one or more non-limiting embodiments.

Water soluble or water dispersible silicone polyethers may also be included in the personal care composition. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

The personal care composition and/or emulsions of the the pituitous silicone fluid may also include a solvent such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials. In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Method of Forming the Personal Care Compositions

This disclosure also provides methods for forming personal care compositions. The methods include combining a personal care product or any other similar compound, as described above, with a pituitous silicone fluid, or with an emulsion of pituitous silicone fluid. It is contemplated that the personal care product may be present before, during, and/or after reaction of the first linear organopolysiloxane and the second linear organopolysiloxane. In on embodiment, the pituitous fluid is prepared individually and then combined later with the personal care composition ingredients. It is possible to include some personal care ingredients at a fluid reaction step (i.e., formation of the hydrosilylation reaction product) but various factors may need to be controlled such as reaction inhibition, temperature sensitivity of the ingredients, etc. Techniques known in the art for formation of personal care formulations, including but not limited to, mixing techniques, cold blends or application of heat to facilitate forming the composition, can be used. The order of addition used herein can be any known in the art.

This disclosure also provides a method of imparting pituitous properties to a carrier fluid. The method includes the step of reacting the first linear organopolysiloxane and the second linear organopolysiloxane via a hydrosilylation reaction in the presence of the hydrosilylation catalyst and the carrier fluid to form the hydrosilylation reaction product including the alkenyl or Si—H functionality. This method may also include one or more method steps as described above.

The present invention can be further illustrated by the following nonlimiting Embodiments.

Embodiment 1

A method for preparing an emulsion of a silicone fluid having pituitous rheological properties, the process comprising:
(A) forming an oil-in-water emulsion by:
  (i) combining a carrier fluid, a SiH-containing organopolysiloxane and an alkenyl-containing organopolysiloxane to form a mixture,
  (ii) adding a surfactant to the mixture, and
  (iii) adding water and mixing to form an oil-in-water emulsion, wherein the mixture of the carrier, the SiH-containing organopolysiloxane and the alkenyl-containing organopolysiloxane forms an oil phase of the oil-in-water emulsion; and
(B) reacting the SiH-containing organopolysiloxane and the alkenyl-containing organopolysiloxane in the oil phase of the emulsion formed in (A)(iii) in the presence of a hydrosilylation catalyst to form an emulsion of a silicone fluid having pituitous rheological properties.

Embodiment 2

The method of Embodiment 1, wherein the alkenyl-containing organopolysiloxane is vinyl terminated.

Embodiment 3

The method of Embodiment 1 or 2, wherein the alkenyl-containing organopolysiloxane is dimethylvinyl terminated.

Embodiment 4

The method of Embodiment 1, wherein the SiH-containing organopolysiloxane has 2 to 10 pendant SiH sites.

Embodiment 5

The method of Embodiment 1, wherein the oil phase comprises from 40% to 80% by weight of the emulsion formed in (A)(iii).

Embodiment 6

The method of any of the preceding Embodiments 1 to 5, wherein the surfactant is non-ionic, cationic, or anionic.

Embodiment 7

The method of any of the preceding Embodiments 1 to 6, wherein the surfactant comprises from 0.01% to 10% by weight of the emulsion formed in (A)(iii).

Embodiment 8

The method of any of the preceding Embodiments 1 to 7, wherein the molar ratio of vinyl:SiH is from 0.01 to 10.

Embodiment 9

The method of any of the preceding Embodiments 1 to 8, wherein the carrier fluid comprises 5% to 80% by weight of the emulsion of a silicone fluid having pituitous rheological properties.

Embodiment 10

The method of any of the preceding Embodiments 1 to 9, wherein the carrier fluid is a silicone fluid, an organic solvent, an organic oil, or any combination thereof.

Embodiment 11

The method of any of the preceding Embodiments 1 to 10, wherein the silicone fluid comprises a branched organopolysiloxane.

Embodiment 12

The method of any of the preceding Embodiments 1 to 11, wherein the pituitous rheological properties of the silicone fluid are determined from a plot of normal stress in Pascals vs a perpendicular shear rate in $\sec^{-1}$ wherein the plot has an average slope that is greater than 3.6.

Embodiment 13

The method of any of the preceding Embodiments 1 to 12, wherein the emulsion of a silicone fluid having pituitous rheological properties further comprises a silicone resin and/or silicone elastomer.

Embodiment 14

The method of Embodiment 11, wherein the silicone resin is an MQ resin.

Embodiment 15

The method of Embodiment 11, wherein the silicone resin is a resin having T and/or Q units.

Embodiment 16

The method of Embodiment 13, wherein the resin having Q units comprises:
(1) one or more Q units of the formula $(SiO_{4/2})$;
(2) from 15 to 995 D units of the formula $R^b{}_2SiO_{2/2}$ which units (1) and (2) may be inter-linked in any appropriate combination; and
(3) M units of the formula $R^a R^b{}_2 SiO_{1/2}$, wherein each $R^a$ substituent is selected from the group consisting of an alkyl group having from 1 to 6 carbon atoms, an alkenyl group having from 1 to 6 carbon atoms and an alkynyl group having from 1 to 6 carbon atoms, at least three $R^a$ substituents in the branched siloxane being alkenyl or alkynyl units, and each $R^b$ substituent is selected from the group consisting of an alkyl group having from 1 to 6 carbon atoms, an alkenyl group having 2 to 6 carbon atoms, an aryl group, an alkoxy group, an acrylate group and a methacrylate group.

Embodiment 17

The method of Embodiment 14, wherein the resin having Q units is prepared by equilibrating
a) tetrakis(vinyldimethylsiloxy)silane, and
b) dimethyl cyclic siloxanes,
wherein the weight ratio of b:a is at least 99:1.

Embodiment 18

The emulsion of a silicone fluid having pituitous rheological properties prepared according to any of the preceding Embodiments 1 to 17.

Embodiment 19

A personal care composition comprising the emulsion prepared by any one of Embodiments 1 to 17.

Embodiment 20

The personal care composition of Embodiment 19, wherein the personal care composition is a hair shampoo, a hair conditioner, a hair treatment composition, or a skin care composition.

Having described the invention with reference to certain embodiments, other embodiments will become apparent to one skilled in the art from consideration of the specification. The invention is further defined by reference to the following examples describing the preparation of the emulsions and processes of the invention. It will be apparent to those skilled in the art that many modifications, both to materials and procedures, may be practiced without departing from the scope of the invention.

EXAMPLES

The following Examples are provided so that one skilled in the art will more readily understand the invention. Unless otherwise indicated, all parts and percents are by weight and all viscosities are at 25° C. Viscosity measurements of the polymer products were carried out using a a Brookfield Viscometer, spindle 6, 10 rpm. All Particle size values were determined using a Malvern Mastersizer 2000.

Example 1 Emulsion of a Silicone Fluid Having Pituitous Rheological Properties Using Non-Ionic Surfactant To a 50 gram maximum dental mixer cup, 25.00 grams of a blend (comprised of 6.22% a vinyl-terminated organopolysiloxane (MW 702,000, and DP about 9461), 0.07% of a trimethylsilyl-terminated dimethyl methylhydrogen organopolysiloxane copolymer (viscosity of 10 cP, MW 1330, and DP about 18), and 93.68% polydimethylsiloxane volatile carrier (dodecamethylpentasiloxane), 1.04 grams of Brij L4, and 1.15 grams of Brij L23 were added. The cup was mixed using a DAC-150 SpeedMixer® for 30 seconds at maximum speed (3450 rpm). 3.01 grams of initial water was then added and again mixed at maximum speed for 30 seconds. To this, 0.02 grams of a Pt catalyst as an organoplatinum complex dispersed in vinyl-terminated organosiloxane (viscosity 400 cP) was added and the cup was put in an oven. The reaction cure began on the addition of the Pt catalyst. Malvern Mastersizer 2000 particle size measurement showed a Dv50=1.218 um.

Example 2 Emulsion of a Silicone Fluid Having Pituitous Rheological Properties Using Cationic Surfactant To a 2.5 oz. squat jar, 15.00 grams of a blend (comprised of 6.22% vinyl-terminated organopolysiloxane (MW 702 000, and DP about 9461), 0.07% of a trimethylsilyl-terminated dimethyl methylhydrogen organopolysiloxane copolymer (viscosity of 10 cP, MW 1330, and DP about 18), and 93.68% polydimethylsiloxane volatile carrier), 2.68 grams of Arquad 16-29, and 12.33 grams of water were added. The jar contents were sheared with a Misonix Sonicator S-4000 at 80% for 2 minutes. To this, 0.02 grams of a Pt catalyst as organoplatinum an complex dispersed in vinyl-terminated organosiloxane (viscosity 400 cP) was added and the cup was put in an oven. The reaction cure began on the addition of a Pt catalyst. Malvern Mastersizer 2000 particle size measurement showed a Dv50=1.749 um.

Example 3 Emulsion of a Silicone Fluid Having Pituitous Rheological Properties Using Anionic Surfactant To a 2.5 oz. squat jar, 20.00 grams of a blend (comprised of 6.22% vinyl-terminated organopolysiloxane (MW 702 000, and DP about 9461), 0.07% a trimethylsilyl-terminated dimethyl methylhydrogen organopolysiloxane copolymer (viscosity of 10 cP, MW 1330, and DP about 18), and 93.68% polydimethylsiloxane volatile carrier), 1.68 grams of Rhodapex ESC-3/A2, 0.8 grams of Brij 30, and 17.51 grams of water were added. The jar contents were sheared with a Misonix Sonicator S-4000 at 80% for 2 minutes. To this, 0.02 grams of a Pt catalyst as an organoplatinum complex dispersed in vinyl-terminated organosiloxane (viscosity 400 cP) was added and the cup was put in an oven. The reaction cure began on the addition of the Pt catalyst. Malvern Mastersizer 2000 particle size measurement showed a Dv50=1.042 um.

Example 4 Characterization of Emulsion of a Silicone Fluid Having Pituitous Rheological Properties In order to characterize the obtained emulsion we used a texture analyzer that helps to define the stickiness, stringiness and work of adhesion when using a dried emulsion. In few words this apparatus is a probe that is able to measure the force needed to pull materials that are sticky and form strings. It goes down and gets in touch with the dried film. Once in touch it goes up at a defined speed. Various parameters that are then used to characterize the prototypes. The cylindrical probe applies a force equals to 6 grams on the sample surface and holds it for 10 seconds in order to let time to the sample to reorganize itself and then the probe goes up. The stickiness is recorded as the maximum force required to separate the sample from the probe whereas the stringiness is the distance the probe moves away from the sample before the force drops to 5 grams. The texture analyzer can also measure the work of adhesion and the hardness. The results are shown in FIG. 1.

Example 5 Variation of the Ratio SiH:Vi With the Level of Carrier

Figure 2:
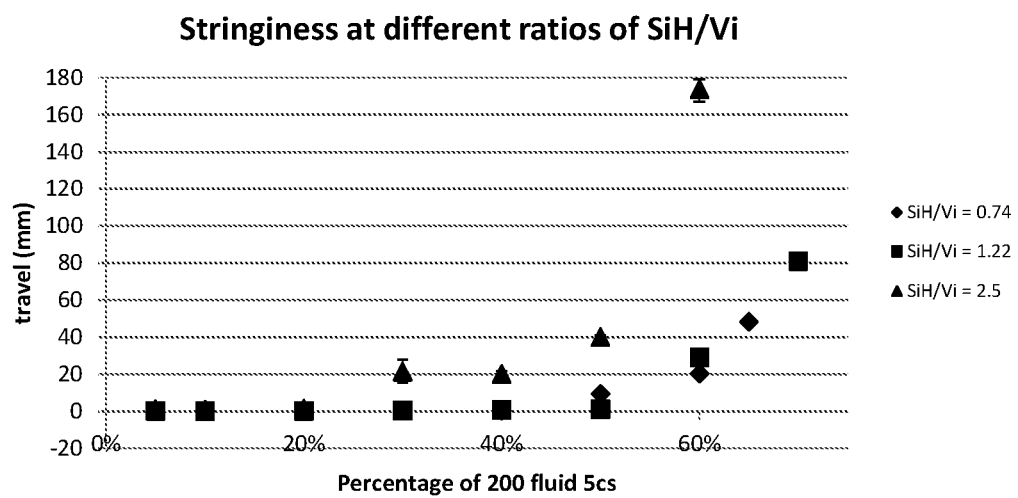
FIG. 2 shows that for different ratio of SiH:vinyl the film formed from dry emulsions tend to develop stringiness starting from 40% of solvent.

In this example, the following materials were used: polydimethylsiloxane (dimethyl siloxane, trimethylsiloxy-terminated) as a carrier, a vinyl-terminated organopolysiloxane (viscosity 55,000 cps, MW 62,000, and DP about 830) as the vinyl-containing specie, and a trimethylsilyl-terminated dimethyl methylhydrogen organopolysiloxane copolymer (viscosity of 10 cP, MW 1330, and DP about 18) as a crosslinker. The emulsion was prepared as follows. The oily phase, i.e., the carrier, SiH– and vinyl-containing molecules are first mixed together. Then nonionic surfactants (Brij LT3 and Brij LT23) were added to the system to get a thick phase. Then using a high shear device (dental mixer) and through addition of water a oil in water emulsion is obtained. Once done, a Pt catalyst (as an emulsion of Pt-4 complexes) was added to the system. It was reacted for 1 day at room temperature. Biocides were added at the end of the process, i.e., phenoxyethanol. Typical formulation composition: oil phase about 60% (mixture of carrier fluid, vinyl functional PDMS and SiH containing ingredient), Brij LT3 2%, Brij LT23 2%. FIG. 2 shows that for different ratio film formed from dry emulsion tend to develop stringiness starting from 40% of solvent.

Example 6 Variation of the Solvent Type

Figure 3:
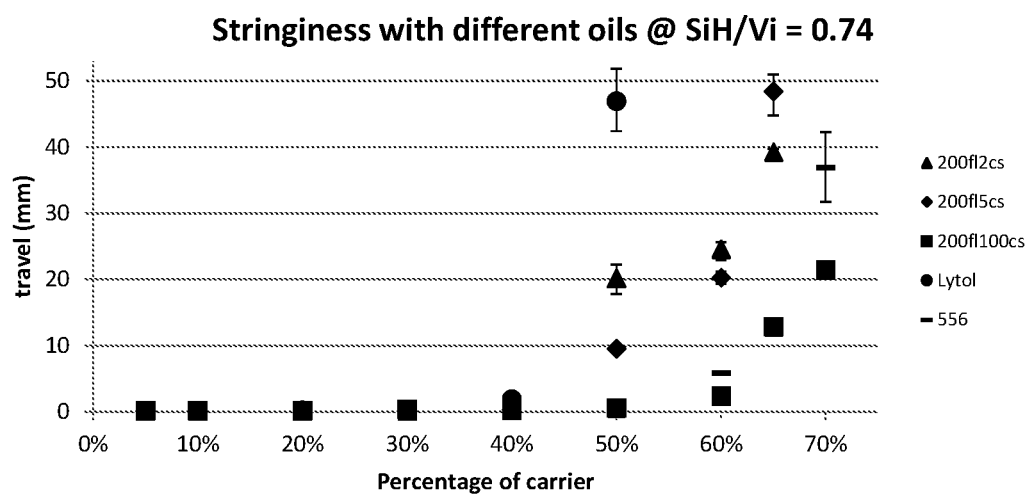
FIG. 3 shows the stringiness effect using different solvents.

In this example, the stringiness effect using different solvents was studied. Various solvents were assessed and the stringiness can be developed regardless of the solvent type. The results are shown in FIG. 3.

Example 7: Effect on Stringiness of Vinyl Molecular Weight

Figure 4:
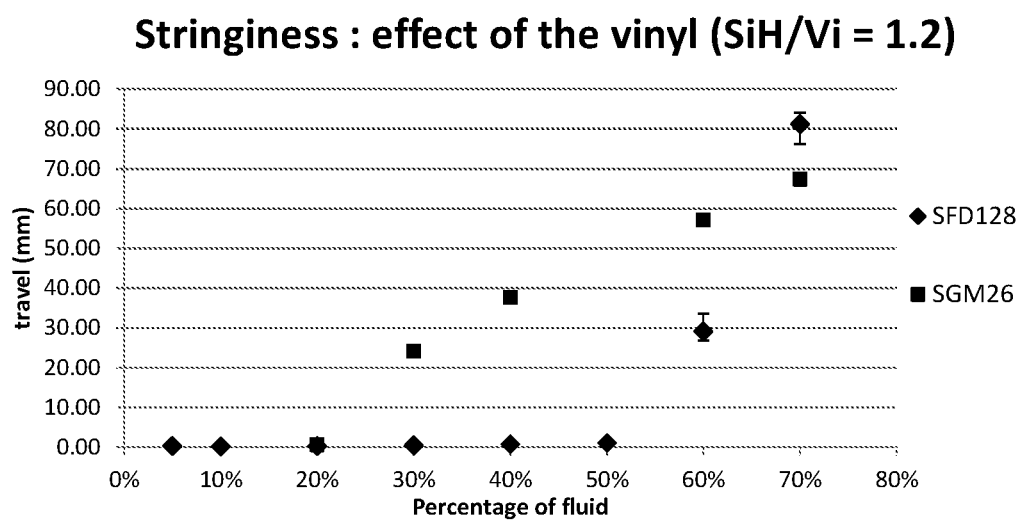
FIG. 4 shows the effect on stringiness by the molecular weight of vinyl-functionalized organopolysiloxane.

Two types of vinyl-functionalized materials were used as follows: a vinyl-terminated organopolysiloxane (MW 702,000, and DP about 9461) and a vinyl-terminated organopolysiloxane (viscosity 55,000 cps, MW 62,000, and DP about 830). The crosslinker was a trimethylsilyl-terminated dimethyl methylhydrogen organopolysiloxane copolymer (viscosity of 10 cP, MW 1330, and DP about 18). The results are shown in FIG. 4.

Example 8: Impact of Additives on Stringiness

Figure 5:
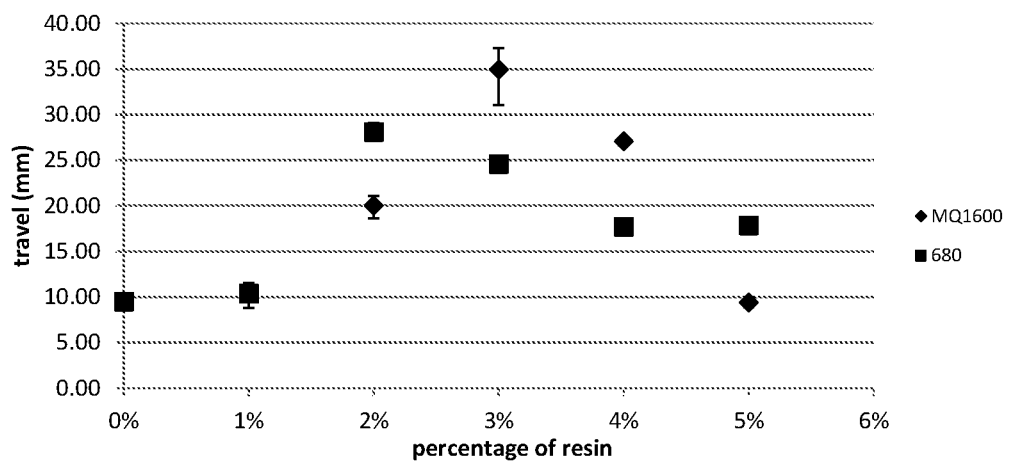
FIG. 5 shows the impact of resins on stringiness.

An emulsion of pituitous silicone fluid was formed in the presence of silicone resins. After formation, a sample of the emulsion was dried and the film monitored for its stringiness ability. Adding some resins accentuated the pituitous behavior. The formulation used was the following: emulsion (50% polydimethylsiloxane carrier, SiH/Vi=0.74 (vinyl-terminated organopolysiloxane (viscosity 55,000 cps, MW 62,000, and DP about 830); a trimethylsilyl-terminated dimethyl methylhydrogen organopolysiloxane copolymer (viscosity of 10 cP, MW 1330, and DP about 18)) with a methyl silsequioxane, hydroxyl-terminated resin or a propyl silsesquioxane, hydroxyl-terminated resin. Results are shown in FIG. 5.

Figure 6:
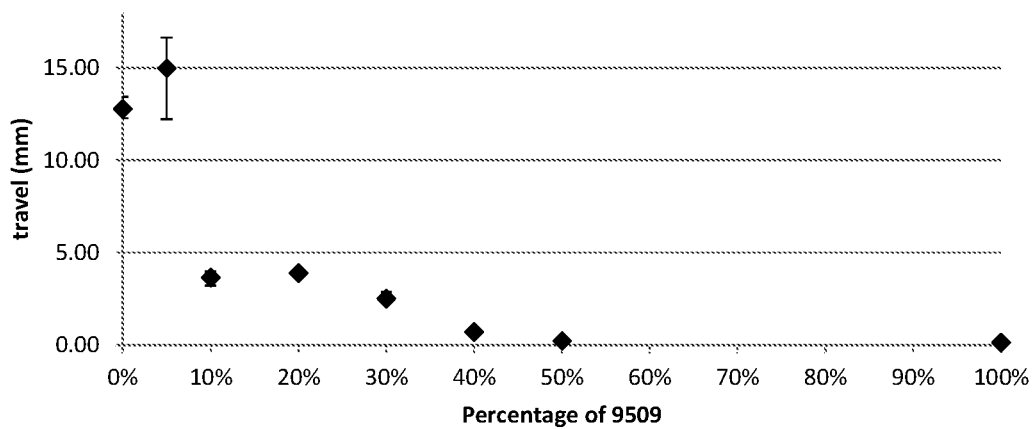
FIG. 6 shows an emulsion of a pituitous silicone fluid with elastomeric dispersion.

Example 9 Mixture of the Pituitous Emulsion Together With Elastomeric Dispersion Emulsion of pituitous silicone fluid (60% polydimethylsiloxane carrier, SiH/Vi=0.74) with addition of a silicone elastomer suspension were prepared. This emulsion showed reduced stringiness. The results are shown in FIG. 6. However when comparing this result versus a linear high molecular weight emulsion (emulsion containing carrier fluids and silicone fluids that comprise a hydrosilylation reaction product of two linear organopolysiloxanes with a viscosity equal to 7000 cP) mixed with the same elastomeric dispersion, the films have a different mechanical behavior. The one containing an emulsion with carrier fluids and silicone fluids that comprise a hydrosilylation reaction product of two linear organopolysiloxanes with a viscosity equal to 7000 cP appearerd less elastic than the pituitous silicone fluid containing one.

Example 10 Rub Off Resistance

Figure 7:
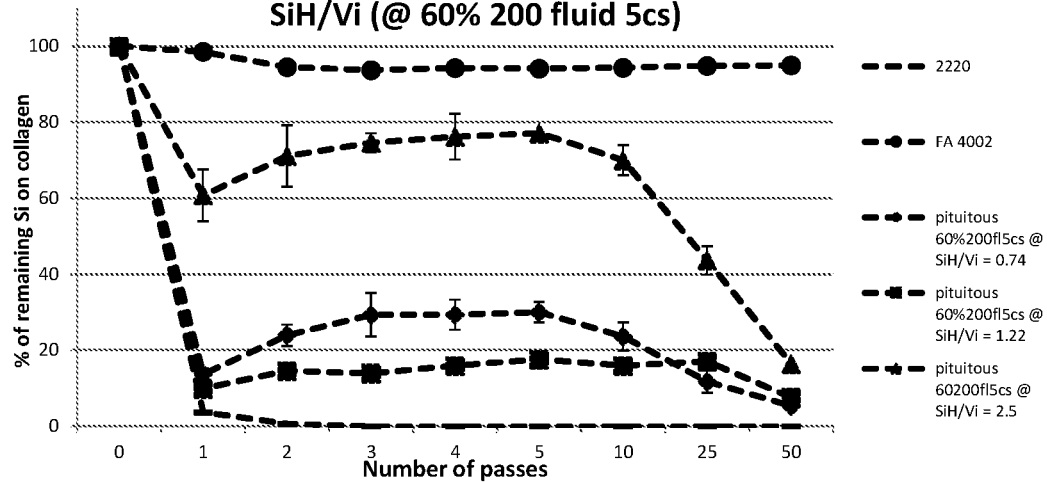
FIG. 7 shows the rub-off resistance of a film formed from an emulsion of a pituitous silicone fluid.

A film is coated on collagen and punched out (diameter of 22 mm) before being fixed on a XRF holder using double-sided tape. Firstly, the initial content in silicon (g/m$^2$) is measured by XRF. The coating is then put on the felt band and exposed to friction using the Braive Washability Tester. The intensity of the friction is controlled by the number of passes on the felt band. After each pass, the residual content in silicon is measured by XRF. In this test we show that while the silicone acrylate chemistry delivers some strong rub off benefits it shows the pituitous fluid can also have interesting performances versus a linear high molecular weight emulsion. The results are shown in FIG. 7.

Example 11 Laundry Application

A foam is a dispersion of gas bubbles in a liquid, solid or gel. The diameter of the air bubbles could exceed 1 μm but the thickness of the lamellae between the bubbles is often in the colloidal size range. An antifoam which prevents the formation of foam, acts on the contact point between three bubbles called vortex. The main properties of effective antifoam are: the insolubility and the ability to be dispersed in the continuous media and the surface tension between the antifoam and the air must be lower than the one between the solution and the air. As the pituitous emulsions have a specific rheological profile they will be able to reach the air water interface without being re-dispersed by the surfactant solution. Hence they could possibly have interesting antifoam properties in laundry application.

The emulsion at 50% of polydimethylsiloxane carrier and with a ratio SiH/Vi=1.0 was formulated with 3% of a methyl silsequioxane, hydroxyl-terminated resin. The SiH fluid and the vinyl polymer were a trimethylsilyl-terminated dimethyl methylhydrogen organopolysiloxane copolymer (viscosity of 10 cP, MW 1330, and DP about 18) and a vinyl-terminated organopolysiloxane (viscosity 55,000 cps, MW 62,000, and DP about 830), respectively. The antifoam performance evaluation was based on the Reckitt Benckiser test and the settings were:

No load

Blank/color program (2h17)

90° C. at 600 rpm

15 L of water at 70 FH (addition of 32 mL of Ca2+ and 135 mL of Mg2+)

80 g of regular powder, and

One rinse at 40° C. at 600 rpm.

Figure 8:
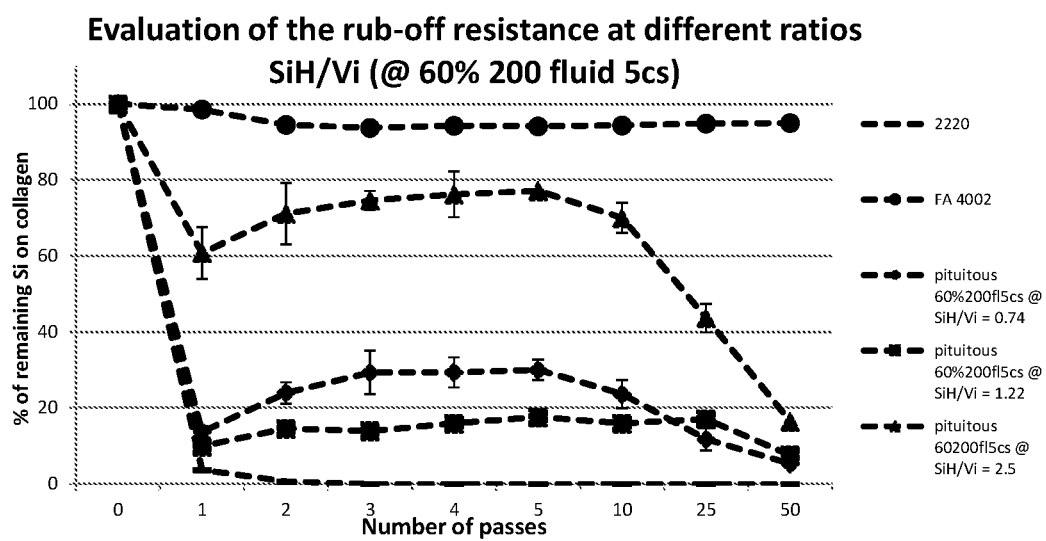
FIG. 8 shows the performance test of emulsions having pituitous silicone fluids as an antifoam agent.

In a first trial, 0.2% of active pituitous emulsion was sprayed directly on the washing powder. Using this powder we showed that this material can act as an antifoam, even though the maximum level of foam is reached earlier than the reference antifoam used by Reckitt Benckiser. Different levels of hydrophobic silica were dispersed in the oil phase using the dental mixer prior to the emulsification step. The presence of silica particles needed an increase in the level of surfactants (11%) in order to get the phase inversion for emulsification. Adding silica to the pituitous emulsion greatly improved the antifoam performance. At 3% silica the granule effectiveness is better than the reference. The results are shown in FIG. 8. Additional testing was carried out in complete wash cycle with a granulated pituitous emulsion. The granule is composed of a carrier, a binder and an active agent. The pituitous silicone emulsion (non-volatile vontent (NVC)=40%) was mixed in equal proportion with the copolymer maleic acid/acrylic acid which acts as a binder before the addition to the zeolite.

|  | Final composition (%) |
| --- | --- |
| maleic acid/acrylic acid copolymer @ 40% | 8.93 |
| Pituitous silicone fluid emulsion (NVC = 40%) | 8.95 |
| Zeolite | 82.12 |
| Total | 100.00 |

Figure 9:
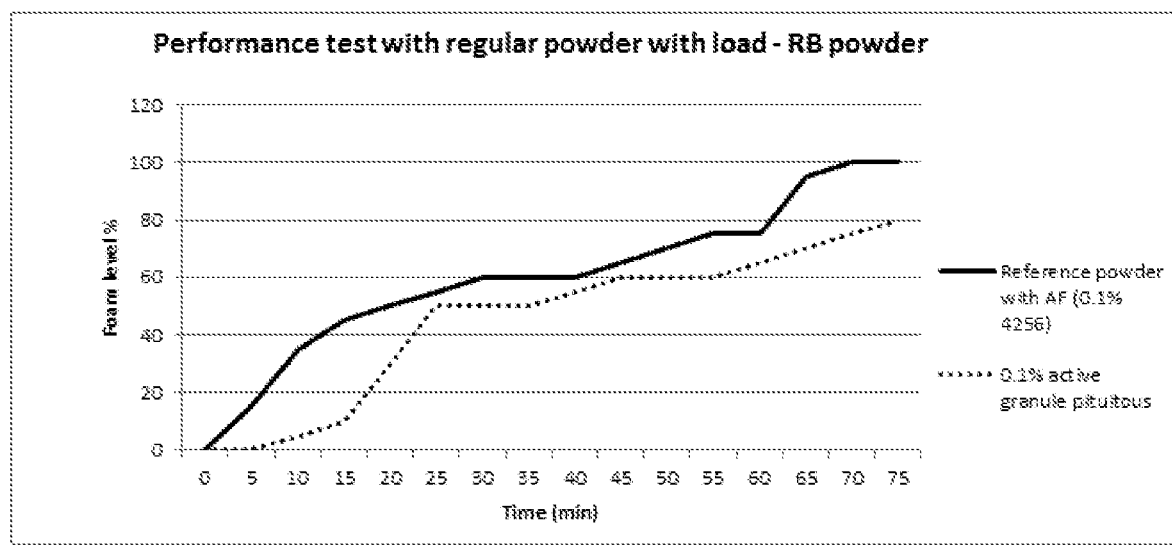
FIG. 9 shows the performance test of a granulated emulsion having a pituitous silicone fluid as an antifoam agent.

The blend was mixed until homogenous and then dried for 20 minutes at 60° C. The silicone granules were sieved between 200 and 1400 mm. The pituitous emulsion used for this testing was composed of:
- 50% polydimethylsiloxane carrier
- 50% vinyl-terminated organopolysiloxane (viscosity 55,000 cps, MW 62,000, and DP about 830)
- 3% trimethylsilyl-terminated dimethyl methylhydrogen organopolysiloxane copolymer (viscosity of 10 cP, MW 1330, and DP about 18)
- 3% a methyl silsequioxane, hydroxyl-terminated resin
- 3% silica Pituitous silicone emulsions show the ability, when provided in granulated form, to affect the foam profile in a more efficient way than a commercial reference granules. The results are shown in FIG. 9.

Example 12 Fabric Care

Fabric softeners help the consumer preserve the new clothes look after the laundering process and the addition of silicones brings consumer benefits by enhancing softness. Due to their physical properties, silicones lubricate the fibers and give softness to fabric. The softeners are more effective when pendant amine groups are introduced to the siloxane backbone. The positively charged quats have a great affinity for the surface fibers because of their globally negative charge. Due to their physical properties and even though they are non-ionic emulsions, pituitous silicone fluids are good candidates as fabric softeners. Pituitous silicone emulsions were mixed with a prototype fabric conditioner developed by KAO Corporation, which is a solution of esterquats, for 24 hours in order to bring charges. The test was then performed with a Miele WM W377 using Dash powder at 40° C. and at 600 rpm. The water hardness is set to 0° FH. Then, the test fabric, which are little terry towels, were line dried overnight before being tested by 16 panelists who have to find and assign a softness score for the towels, the reference being equal to 5. Two types of pituitous silicone emulsions having a vinyl-terminated organopolysiloxane (viscosity 55,000 cps, MW 62,000, and DP about 830) or a vinyl-terminated organopolysiloxane (MW 702,000, and DP about 9461) were tested. The composition of the emulsions as percent by weight are as follows.

| | | |
| --- | --- | --- |
| % polydimethylsiloxane carrier | 60.0 | 60.0 |
| % vinyl-terminated organopolysiloxane (viscosity 55,000 cps, MW 62,000, and DP about 830) | 38.8 | 0.0 |
| % vinyl-termiated organopolysiloxane (MW 702,000, and DP about 9461) | 0.0 | 39.8 |
| % trimethylsilyl-terminated dimethyl methylhydrogen organopolysiloxane copolymer (viscosity of 10 cP, MW 1330, and DP about 18). | 1.2 | 0.2 |
| Molar ratio SiH/Vi | 1.0 | 1.0 |

Figure 10:
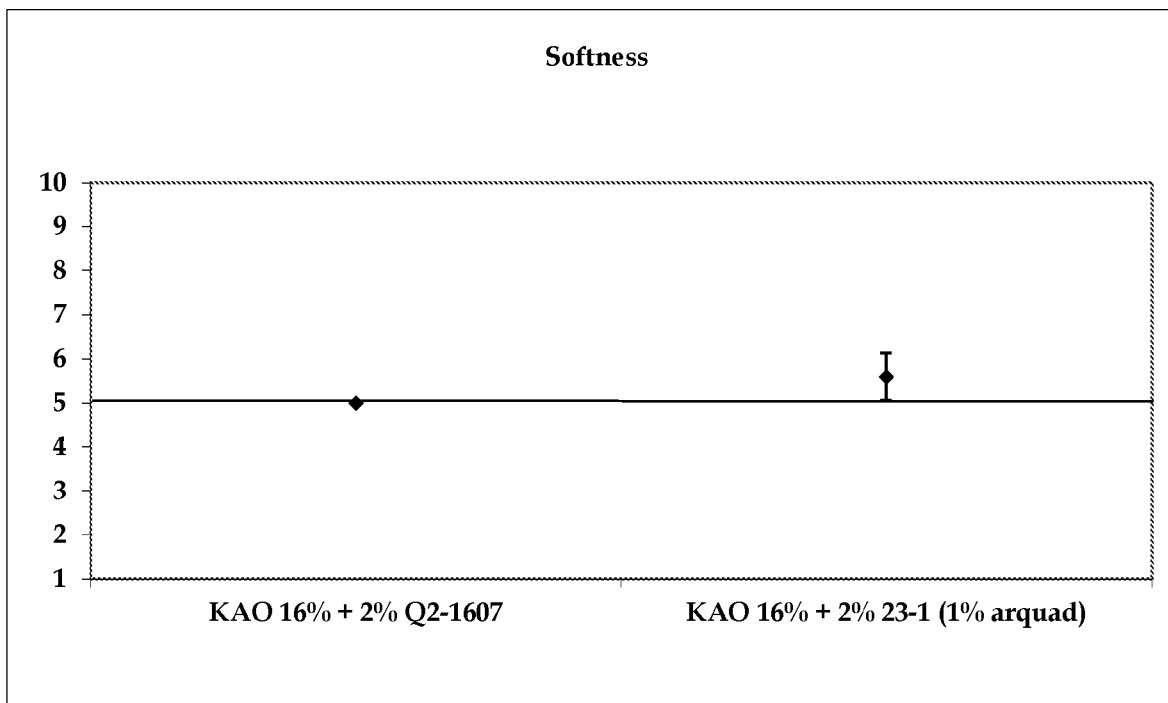
FIG. 10 shows the results of sensory feel by panelist on fabric treated with emulsions having pituitous silicone fluids.

The two pituitous silicone emulsions perform at least as well as the reference if not better (see FIG. 10). Moreover, emulsions using the vinyl polymer of highest molecular weight seems to give better results. Further testing was done versus the fabric care reference emulsion containing dimethyl siloxane with methyl silsesquioxane, hydroxyl-terminated at 2% active level. To improve the deposition on the fabric, 1% of Arquad 16-29 was added to the pituitous silicone emulsions and the first testing having the two vinyl polymers was repeated. As the results were similar, the focus was on the polymer with the lowest molecular weight because of its ease to formulate. The next step consisted of checking the impact of the carrier viscosity. Therefore, two additional pituitous silicone emulsions using the vinyl-terminated organopolysiloxane (viscosity 55,000 cps, MW 62,000, and DP about 830) as vinyl polymer were tested, one using the polydimethylsiloxane carrier and the other using the polydimethylsiloxane volatile carrier. As the latter one gave promising results, it was then compared to reference emulsion containing dimethyl siloxane with methyl silsesquioxane, hydroxyl-terminated resin. The results were similar even though several panelists felt a nicer sensory in favor of the pituitous silicone emulsion (see FIG. 10).

|  | Average | LCL | UCL | E | No. of panelist |
| --- | --- | --- | --- | --- | --- |
| KAO 16% + 2% of emulsion containing dimethyl siloxane with methyl silsesquioxane, hydroxyl-terminated | 5 | 5 | 5 | 0 | 5 |
| KAO 16% + 2% 23-1 (1% arquad) | 5.59375 | 4.939683 | 6.247817 | 0.654067 | 11 |

Confidence interval at 95%,
LCL = lower control limit,
UCL = upper control limit,
E = error Example 13 Skin Care Application A W/O (water in oil) cream was formulated with either a pituitous silicone emulsion (60% of carrier, SiH/Vi=1.0), or a pituitous silicone fluid (a lightly crosslinked high MW polymer in a volatile dimethicone carrier fluid). The combination of the carrier fluid and the hydrosilylation reaction product provide the pituitous silicone fluid with a viscosity, measured in Pascal seconds (Pa·s) and collected relative to the shear rate in sec$^{-1}$, from 0.1 to 75 Pa·s, from 0.3 to 15 Pa·s, from 0.5 to 5, or from 1 to 3 Pa·s). Sensory evaluations were performed on 18 panelists in a climate controlled room where the humidity and the temperature were controlled (RH=50%, T=25° C.). The pituitous silicone emulsion was compared either to the pituitous silicone fluid or to a control without silicone. The formulation compositions were as follows.

|   | INCI name | % | % | % |
|---|---|---|---|---|
| A | Lauryl PEG-10 Tris(trimethylsiloxy)silylethyl Dimethicone | 3 | 3 | 3 |
|   | Dimethicone | 22 | 22 | 12 |
|   | Pituitous silicone fluid | — | — | 10 |
| B | Water | 66.5 | 66.5 | 68.5 |
|   | Sodium Chloride | 1 | 1 | 1 |
|   | Glycerin | 5 | 5 | 5 |
|   |   | — | 2 | — |
| C | Phenoxyethanol (and) Ethylhexylglycerin | 0.5 | 0.5 | 0.5 |
|   | total | 100 | 100 | 100 |

Figure 11:
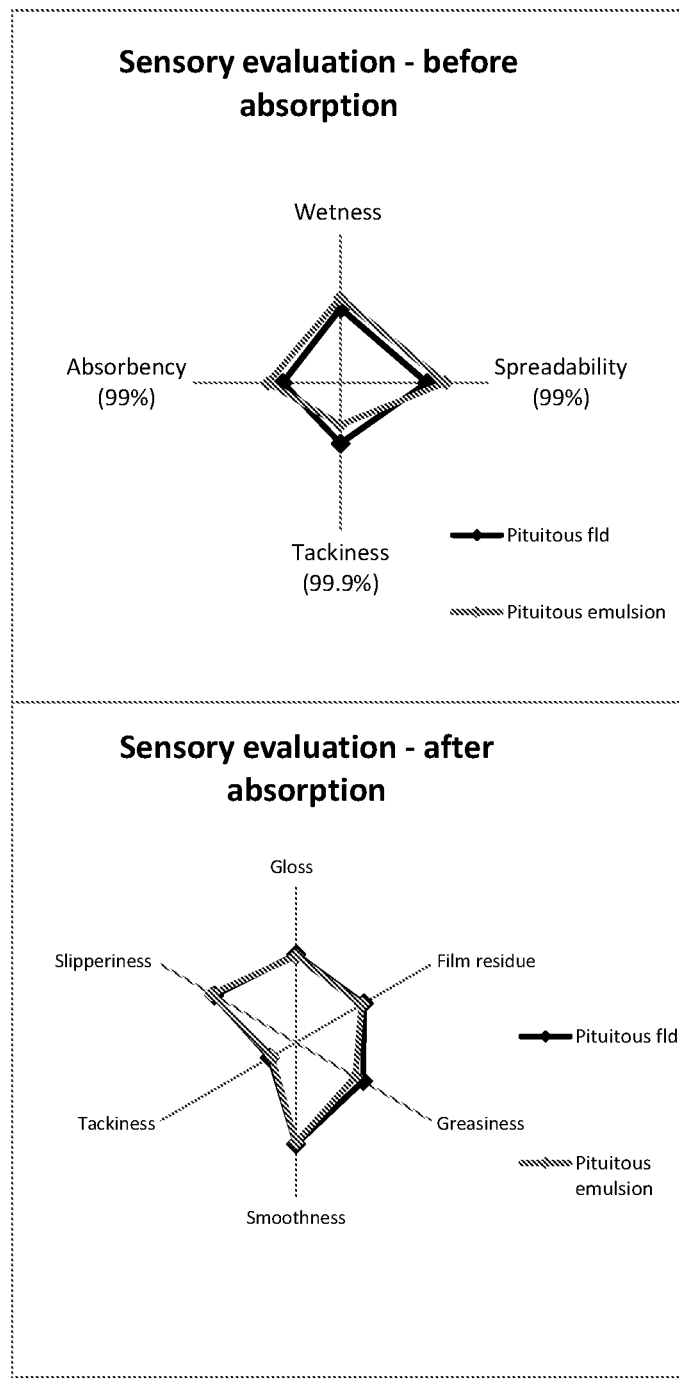
FIG. 11 shows the before and after absorption properties of emulsions having pituitous silicone fluids compared to pituitous silicone fluids.

Pituitous silicone emulsion vs pituitous silicone fluid: Before absorption, the pituitous silicone emulsion has a better absorption and spreadability and is less tacky than the pituitous fluid. However, after absorption, there are no significative differences between the pituitous emulsion and the fluid. The results are shown in FIG. 11.

Figure 12:
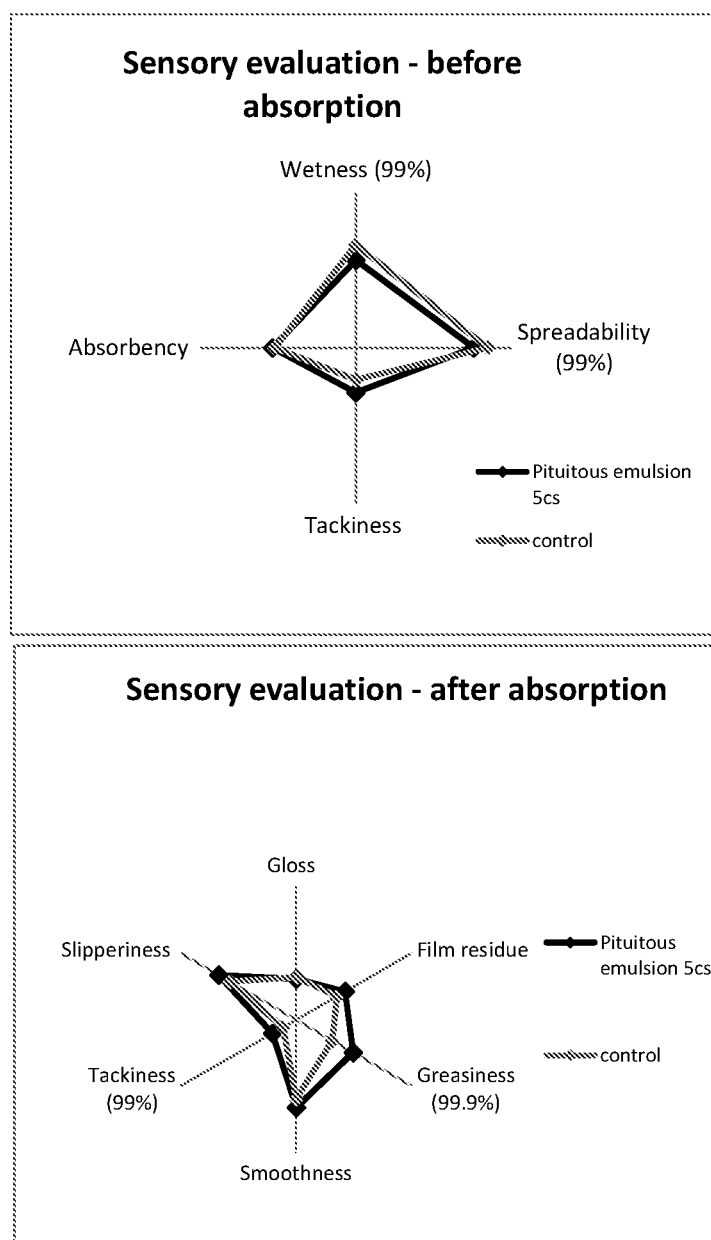
FIG. 12 shows the before and after absorption properties of emulsions having pituitous silicone fluids compared to a control.

Pituitous silicone emulsions vs a control without silicone: Before absorption, the pituitous silicone emulsion was less wet than the control. After absorption, the pituitous silicone emulsion was greasier and tackier than the control. The results are shown in FIG. 12.

Example 14 Pituitous Silicone Emulsion

The following pituitous silicone emulsion was prepared according to the procedure in Example 5. Surfactant 1 was Brij LT23 and surfactant 2 was Brij LT3. The ratio of surfactant 1 to surfactant 2 was 1.15. The total surfactant was 4.41%. The molar ratio was 0.98 (expected molar ratio is 1). DV0.1 was 1.190 μm, DV0.5 was 1.662 μm and DV0.9 was 1.308 μm.

| Ingredients | % |
|---|---|
| polydimethylsiloxane carrier | 42.80 |
| vinyl-terminated organopolysiloxane (viscosity 55,000 cps, MW 62,000, and DP about 830) | 17.27 |
| a trimethylsilyl terminated dimethyl methylhydrogen copolymer having viscosity of 10 cP, MW 1656, and DP 18. | 0.84 |
| Surfactant 1 | 2.34 |
| Surfactant 2 | 2.07 |
| Water | 34.30 |
| Pt catalyst (as an emulsion of Pt-4 complexes) | 0.38 |
| Total | 100.00 |

Example 15 Pituitous Silicone Emulsion

The following pituitous silicone emulsions were prepared for Skin Care Evaluation.

Example 15a

| Ingredients | % |
|---|---|
| Siloxane oligomer vinyl terminated MW11500 and vinyl content of 0.47% | 24.13806976 |
| F1-0049 | 2.413806976 |
| Branching agent, SiH functional, 100 DP and 6SiH functional groups, MW9000, SiH content of 0.066% | 9.447640504 |
| Caprylyl Methicone (40%) | 24.00048276 |
| Tween 20 | 0.6 |
| Tergitol 15S9 | 2.4 |
| Water | 37 |

Example 15b

| Ingredients | % |
|---|---|
| Siloxane oligomer vinyl terminated MW11500 and vinyl content of 0.47% | 20.11427239 |
| F1-0049 | 2.011427239 |
| Siloxane oligomer vinyl terminated MW11500 and vinyl content of 0.47% | 7.874300373 |
| 5 cst siloxane fluid | 30 |
| Tween 20 | 0.6 |
| Tergitol 15S9 | 2.4 |
| Water | 37 |

| Ingredients | Example 15c | Example 15d |
|---|---|---|
| 2 cst siloxane fluid | 21.32% | 21.32% |
| Siloxane oligomer vinyl terminated, MW62000, vinyl content of 0.088% | 8.88% | 8.88% |
| Siloxane oligomer vinyl terminated MW11500 and vinyl content of 0.47% | 0.26% | 0.26% |
| Brij LT23 | 1.20% | 1.20% |
| Brij LT3 | 1.04% | 1.04% |
| Water | 15.74% | 15.74% |
| Water | 51.44% | 51.44% |
| hydrosilylation catalyst | 0.12% | 0.12% |
|   | 100.00% | 100.00% |

Example 16 Formulation for Skin Care Trials

Figure 13:
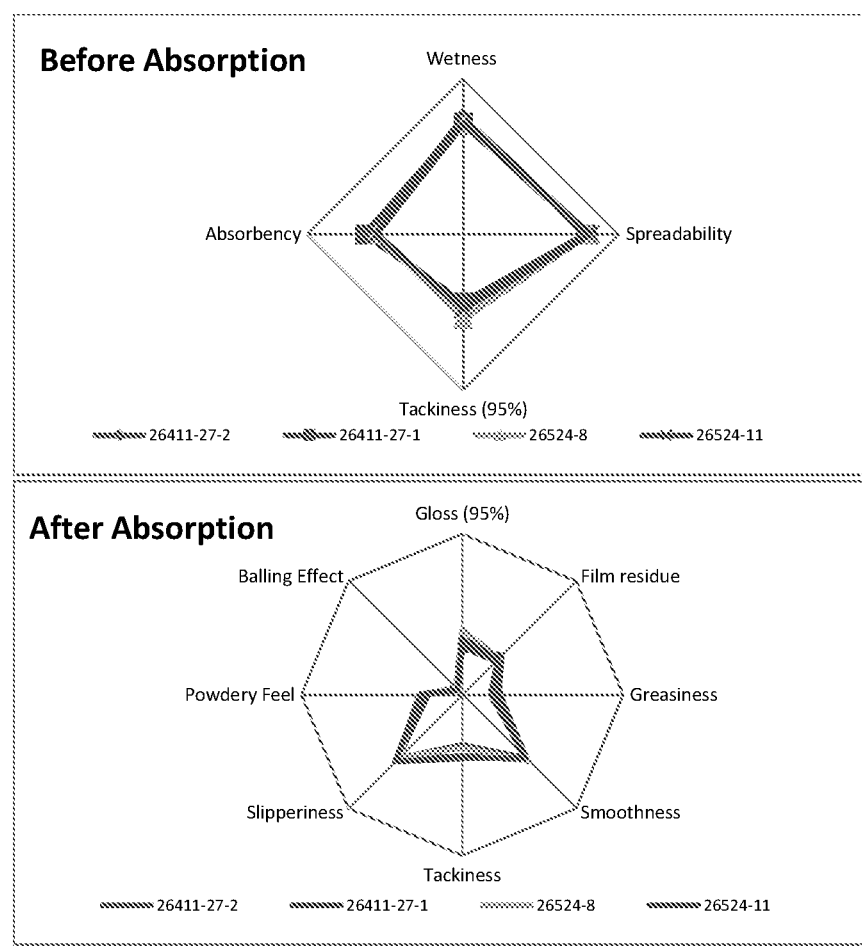
FIG. 13 shows the before and after absorption properties of emulsions having pituitous silicone fluids compared to a control on skin.

Procedure: The phase A ingredients were mixed in the order listed until homogeneous. The performance results are shown in FIG. 13.

| Ingredients | | Suspensions trials | | | | | |
|---|---|---|---|---|---|---|---|
| | | No 1 (%) | No 2 (%) | No 3 (%) | No 4 (%) | No 5 (%) | No 6 (%) |
| Phase A | | | | | | | |
| Water | | 84.80 | 84.80 | 84.80 | 84.80 | 84.80 | 93.10 |
| Glycerin | | 5.00 | 5.00 | 5.00 | 5.00 | 5.00 | 5.00 |
| | Phenoxyethanol (and) Ethylhexylglycerin | 0.60 | 0.60 | 0.60 | 0.60 | 0.60 | 0.60 |
| | Polyacrylamide (and) C13-14 Isoparaffin (and) Laureth-7 | 1.30 | 1.30 | 1.30 | 1.30 | 1.30 | 1.30 |
| Pituitous Emulsion (60%) | Example 15d | 8.30 | — | — | — | — | — |
| | Example 15c | — | 8.30 | — | — | — | — |
| | Example 15b | — | — | 8.30 | — | — | — |
| | Example 15a | — | — | — | 8.30 | — | — |
| High molecular weight siloxane, non-ionic emulsion (60%) | Divinyldimethicone/ Dimethicone Copolymer (and) C12-C13 Pareth-23 (and) C12-C13 Pareth-3 | — | — | — | — | 8.30 | — |
| | | 100.0 | 100.0 | 100.0 | 100.0 | 100.0 | 100.0 |

Example 17 Skin Care Evaluation

Figure 14:
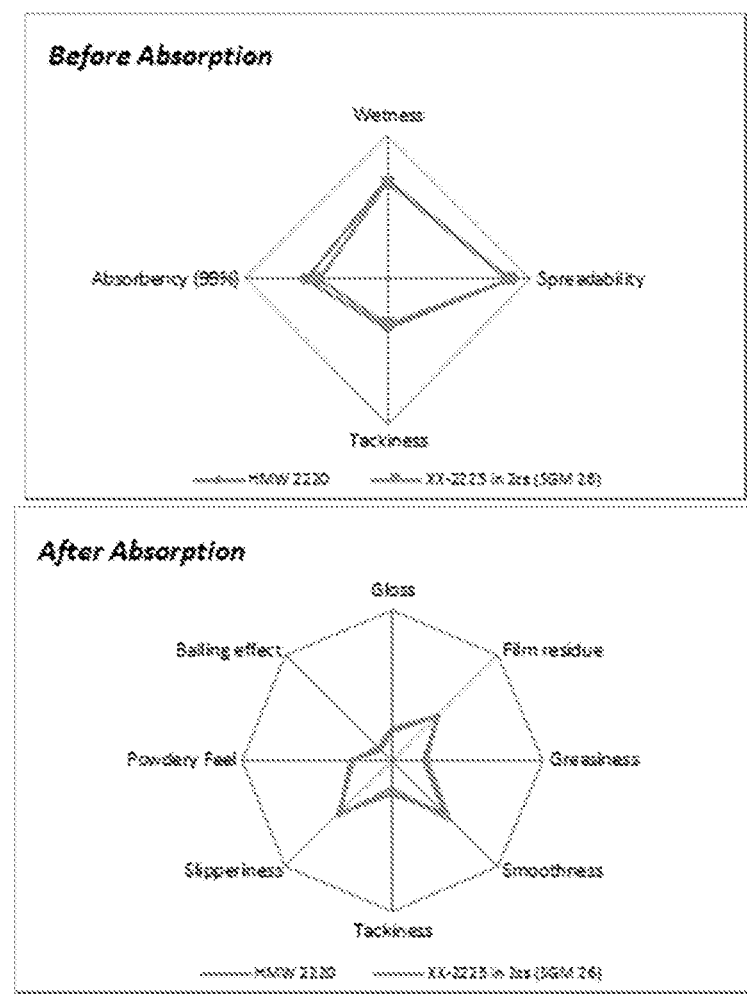
FIG. 14 shows the before and after absorption properties of emulsions having pituitous silicone fluids compared to a control on skin.
Figure 15:
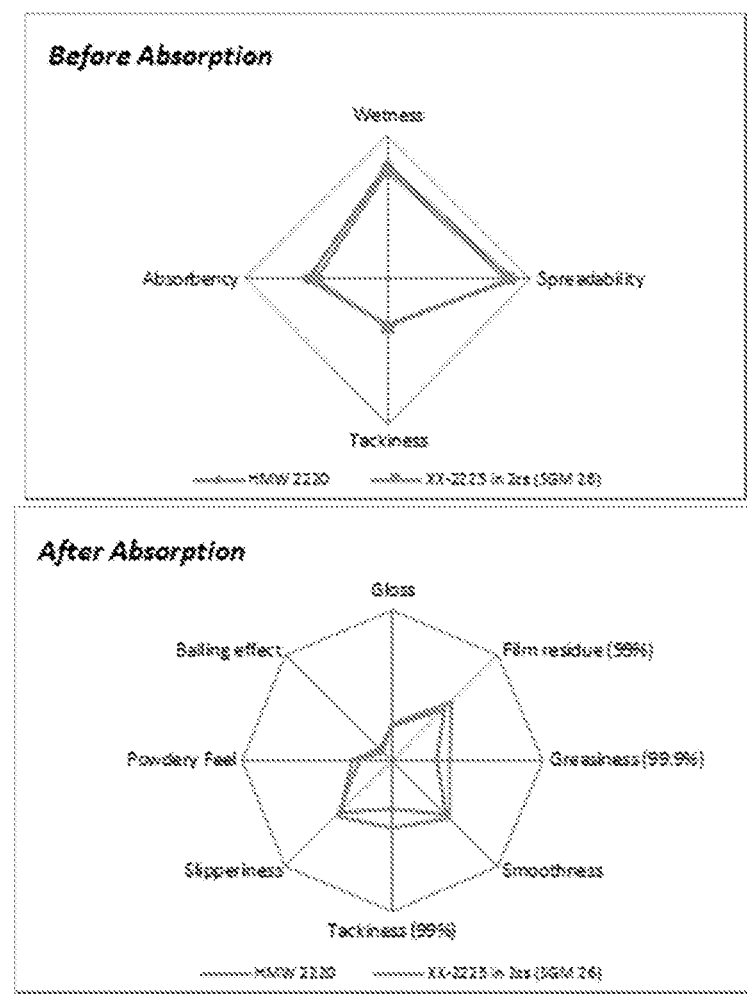
FIG. 15 shows the before and after absorption properties of emulsions having pituitous silicone fluids compared to a control on skin.

Using the same procedure as in Example 16, the following prototypes were made. Results are shown in FIGS. 14 and 15.

| Fluid type | Siloxane fluid 2 cst | Siloxane fluid 5 cst |
|---|---|---|
| siloxane fluid | 36.03% | 36.00% |
| Siloxane oligomer vinyl terminated, MW702000, vinyl content 0.012% | 23.82% | 23.81% |
| Siloxane oligomer vinyl terminated MW11500 and vinyl content of 0.47% | 0.19% | 0.19% |
| Brij L23-69 | 2.82 | 2.83 |
| Brij LT3 | 2.40 | 2.40 |
| % Water | 34.21 | 34.19 |
| hydrosilylation catalyst | 0.54% | 0.57% |
| TOTAL | 100.00 | 100.00 |

Example 18 Hair Care Examples

Figure 16:
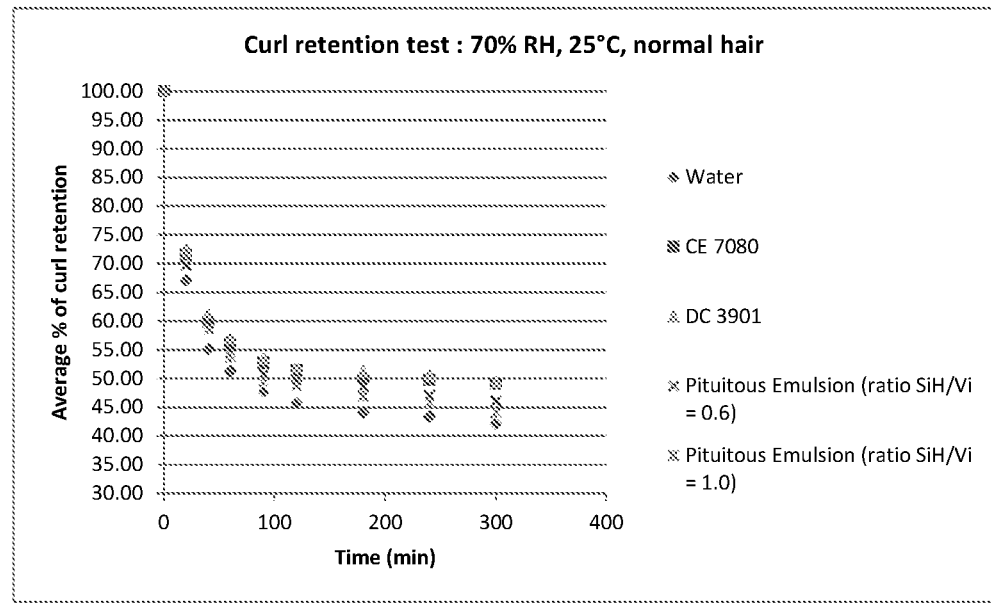
FIG. 16 shows the curl retention results after absorption on normal hair of emulsions having pituitous silicone fluids.

Pituitous Emulsions were also tested as styling agents. The prototypes were tested versus 3901 Liquid Satin Blend and to the CE-7080 smart style which is the reference for styling applications. Curl retention tests were performed in a humidity chamber (70% of relative humidity, 25° C.). 100 mg of each product (diluted at 6% of active material with demineralized water) were spread on swatches and the percentage of curl retention was recorded for 5 hours. Results are shown in FIG. 16. It shows that while leaving a nice feel on the hair swatches some styling properties have been obtained.

| | Siloxane fluid 2 cst | Siloxane fluid 2 cst |
|---|---|---|
| 2 cst siloxane fluid | 36.00% | 36.00% |
| Siloxane oligomer vinyl terminated, MW62000, vinyl content of 0.088% | 23.32% | 22.89% |
| Siloxane oligomer vinyl terminated MW11500 and vinyl content of 0.47% | 0.68% | 1.11% |
| % Brij LT23 | 2.36 | 2.36 |
| % Brij LT3 | 2.05 | 2.05 |
| % Water | 35.28 | 35.09 |
| hydrosilylation catalyst | 0.31% | 0.50% |
| TOTAL | 100.00 | 100.00 |

Example 19 Small Particle Size Pituitous Emulsion

The following pituitous emulsions were prepared having a particle size of 0.3 micron. Particle size of the emulsions in the previous Examples was in the range of 1.5-2.5 microns.

| Ingredients | % for nonionic | % for anionic |
|---|---|---|
| 2 cst. siloxane fluid | 32.99 | 32.98 |
| Siloxane oligomer vinyl terminated, MW62000, vinyl content of 0.088% | 21.27 | 21.27 |
| Branching agent, SiH functional, 100 DP and 6SiH functional groups, MW9000, SiH content of 0.066% | 0.73 | 0.73 |
| Brij L23 | 2.96 | 2.97 |
| Brij L4 | 2.57 | 2.57 |

-continued

| Ingredients | % for nonionic | % for anionic |
|---|---|---|
| Water #1 | 5.09 | 5.09 |
| Dilution Water | 33.74 | 32.74 |
| Rhodapex EST-30/SBL | 0.00 | 1.00 |
| Phenoxyethanol | 0.65 | 0.65 |
| | 100.00 | 100.00 |

Example 20 Application Tests in Laundry Application

A foam is a dispersion of gas bubbles in a liquid, solid or gel. The diameter of the air bubbles could exceed 1 micron but the thickness of the lamellae between the bubbles is often in the colloidal size range. An antifoam which prevents the formation of foam, acts on the contact point between three bubbles called vortex. The main properties of effective antifoam are: the insolubility and the ability to be dispersed in the continuous media and the surface tension between the antifoam and the air must be lower than the one between the solution and the air.

As the pituitous emulsions have a specific rheological profile they will be able to reach the air water interface without being re-dispersed by the surfactant solution. Hence they could possibly have interesting antifoam properties in laundry application. The emulsion at 50% of 200 fluid 5 cSt and with a ratio SiH/Vi=1.0 is formulated with 3% of resin MQ 1600. The SiH fluid and the vinyl polymer are the Q2-5096 and the SFD 128 respectively. The antifoam performance evaluation is based on the Reckitt Benckiser test of which the settings are:

No load
Blank/color program (2h17)
90° C. at 600 rpm
15 L of water at 70 FH (addition of 32 mL of Ca2+ and 135 mL of Mg2+)
80 g of regular powder
One rinse at 40° C. at 600 rpm In a first trial 0.2% of active pituitous emulsion is sprayed directly on the washing powder. Using this powder we showed that this material can act as an antifoam, even though the maximum level of foam is reached earlier than the reference antifoam used by Reckitt Benckiser.

As this result seems promising, different levels of hydrophobic silica Sipernat D10, known to enhance the antifoam activity, have been dispersed in the oil phase using the dental mixer prior to the emulsification step. We noticed that in presence of silica particles we needed to increase the level of surfactants (11%) in order to get the phase inversion thus the emulsification.

When adding silica to the pituitous emulsion the antifoam performance is greatly improved. At 3% the granule effectiveness is better than the reference.

Extra testing have been carried out in complete wash cycle with a granulated pituitous emulsion. The granule is composed of a carrier, a binder and an active agent. The pituitous emulsion (NVC=40%) is mixed in equal proportion with the sokalan CP5 (copolymer maleic acid/acrylic acid) which acts as a binder before the addition to the zeolite.

| | Final composition (%) |
|---|---|
| Sokalan CP5 @ 40% | 8.93 |
| Pituitous emulsion (25833-24-1) (NVC = 40%) | 8.95 |
| Zeolite | 82.12 |
| Total | 100.00 |

The blend is mixed until homogenous and then dried for 20 min at 60° C. Finally, the silicone granules are sieved between 200 and 1400 mm.

The pituitous emulsion used for this testing is composed of:

50% 200 fluid 5 cSt
50% SFD 128
3% Q2-5096
3% MQ 1600
3% D10

Figure 17:
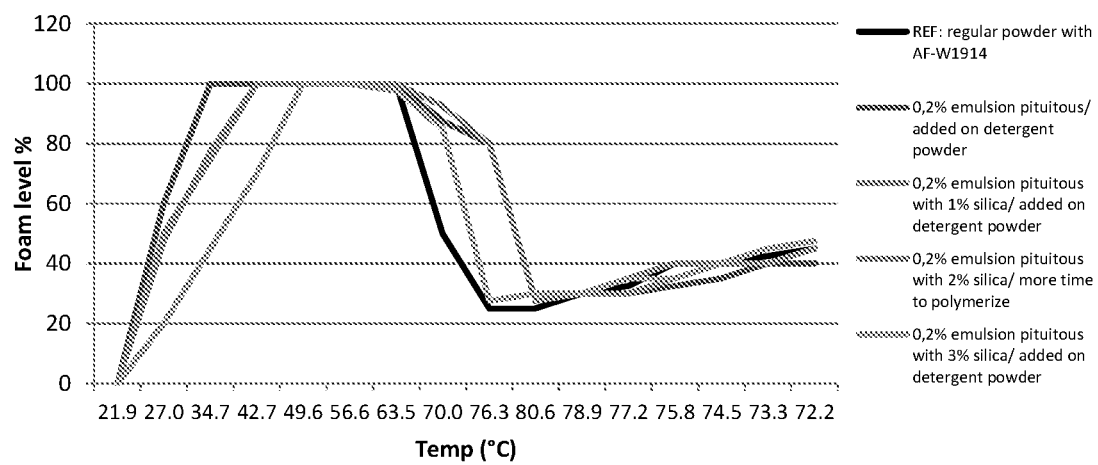
FIG. 17 shows the performance test of pituitous emulsions used as antifoam agent.
Figure 18:
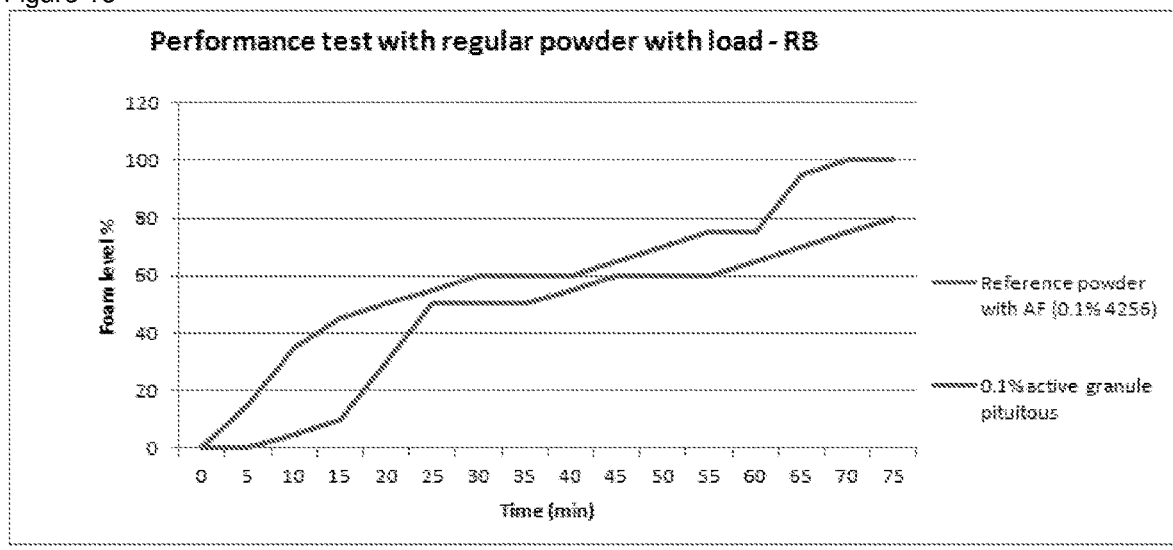
FIG. 18 shows the performance test of the granulated pituitous emulsions used as antifoam agent.

This initial testing using a non-optimised pituitous emulsion is pretty encouraging as it shows the ability of the fluid, once granulated, to affect the foam profile in a more efficient way than a commercial granule would do. The results are shown in FIGS. 17 and 18.

Example 21 Fabric Care

Fabric softeners help the consumer preserve the new clothes look after the laundering process and the addition of silicones brings consumer benefits by enhancing softness. Indeed, thanks to their physical properties, silicones lubricate the fibers and give softness to fabricSt. The softeners are more effective when pendant amine groups are introduced to the siloxane backbone. The positively charged quats have a great affinity for the surface fibers because of their globally negative charge.

Thanks to their physical properties and even though they are non-ionic emulsions, the pituitous can be a good candidate as fabric softeners.

The pituitous emulsions are mixed with a prototype fabric conditioner developed by KAO which is a solution of esterquats for 24 hours in order to bring charges. The test is then performed with a Miele WM W377 using Dash powder at 40° C. and at 600 rpm. The water hardness is set to 0° FH. Then, the test fabricSt which are little terry towels are line dried overnight before being tested by 16 panelists which have to find and quote the softest towels, the reference being equal to 5.

We first tested two types of pituitous emulsions with either the SFD128 or the SGM26. The active levels of these emulsions are:

| % 200 fluid 5 cSt | 60.0 | 60.0 |
|---|---|---|
| % SFD128 | 38.8 | 0.0 |
| % SGM26 | 0.0 | 39.8 |
| % Q2-5096 | 1.2 | 0.2 |
| Molar ratio SiH/Vi | 1.0 | 1.0 |

The two pituitous emulsions provide better softness performance compared to the reference but not in a significant way. Moreover, the emulsion using the vinyl polymer of highest molecular weight seems to give better results.

We then repeated the testing versus the fabric care reference emulsion Dow Corning Q2-1607 emulsion à 2% active level.

| | Average | LCL | UCL | E | Nb of panelist |
|---|---|---|---|---|---|
| KAO 16% + 2% Q2-1607 | 5 | 5 | 5 | 0 | 5 |
| KAO 16% + 2% 23-1 (1% arquad) | 5.59375 | 4.939683 | 6.247817 | 0.654067 | 11 |

Confidence interval at 95%

To improve the deposition on fabric, 1% of Arquad 16-29 is added to the pituitous emulsions and the first testing opposing the two vinyl polymers is repeated. As the results are similar, we decided to focus on the polymer with the lowest molecular weight because of its ease to formulate.

The next step consists on checking the impact of the carrier viscosity. Therefore two pituitous emulsions using the SFD 128 as vinyl polymer are tested, one using either the 200 fluid 5 cSt or the 200 fluid 2 cSt. As the latter one gives promising results, it is then compared to reference emulsion Dow Corning Q2-1607. The results are similar even though several panelists feel a nice sensory in favor of the pituitous emulsion.

Example 22 Skin Care Application

We formulated a W/O cream with either the pituitous emulsion (60% of carrier, SiH/Vi=1.0) or the pituitous fluid (7224). Then, sensory evaluations are performed on 18 panelists in a climatic room where the humidity and the temperature are controlled (RH=50%, T=25° C.). The pituitous emulsion is compared either to the pituitous fluid or to a control without silicone. The formulations composition is:

| | Product name | INCI name | % | % | % |
|---|---|---|---|---|---|
| A | Dow Corning ® 5300 Formulation Aid | Lauryl PEG-10 Tris(trimethylsiloxy)silylethyl Dimethicone | 3 | 3 | 3 |
| | XIAMETER PMX-200 2CS | Dimethicone | 22 | 22 | 12 |
| | Dow Corning ® 2-7224 (6.25% active) | Pituitous fluid | — | — | 10 |
| B | | Water | 66.5 | 66.5 | 68.5 |
| | | Sodium Chloride | 1 | 1 | 1 |
| | | Glycerin | 5 | 5 | 5 |
| | pituitous emulsion (60% active) | | — | 2 | — |
| C | Euxyl PE 9010 | Phenoxyethanol (and) Ethylhexylglycerin | 0.5 | 0.5 | 0.5 |
| | | total | 100 | 100 | 100 |

Example 23 Pituitous Emulsion vs Pituitous Fluid

Figure 19:
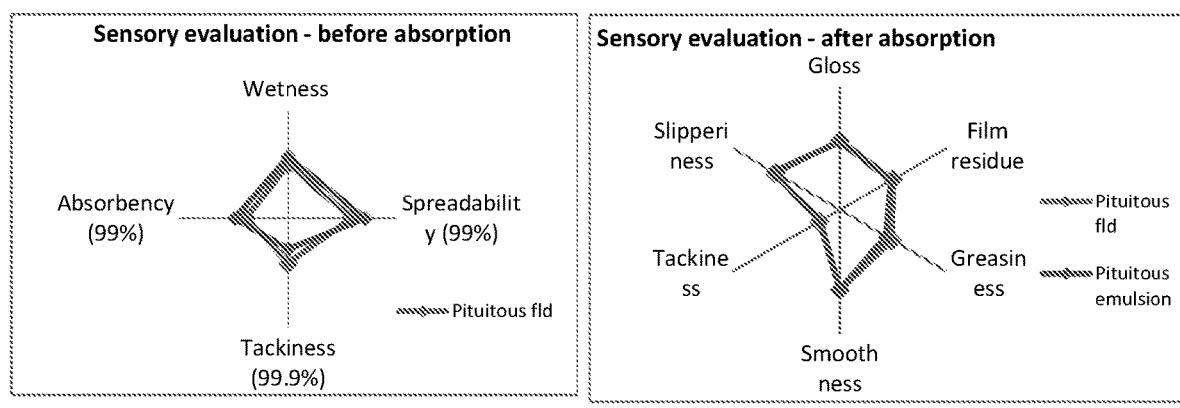
FIG. 19 shows the pituitous emulsion vs pituitous fluid performance.

Before absorption, the pituitous emulsion has a better absorption and spreadability and is less tacky than the pituitous fluid. However, after absorption, there are no significative differences between the pituitous emulsions and the fluid. Results are shown in FIG. 19.

Example 24 Pituitous Emulsions vs a Control Without Silicon

Figure 20:
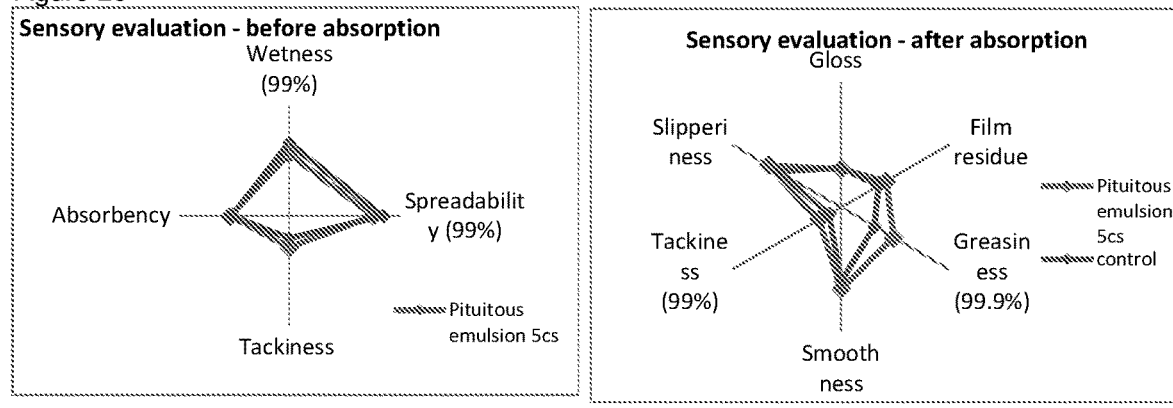
FIG. 20 shows the pituitous emulsions vs a control without silicon performance.

Before absorption, the pituitous emulsions is less wet than the control. After absorption, the pituitous emulsion is greasier and tackier than the control. Results are shown in FIG. 20.

What is claimed is:

1. A method for preparing an emulsion of a silicone fluid having pituitous rheological properties, the process comprising:
(A) forming an oil-in-water emulsion by:
(i) combining a carrier fluid, a linear SiH-containing organopolysiloxane having less than 1 wt % of T and Q units and having a degree of polymerization of from 8 to 500 and an alkenyl-containing organopolysiloxane having a degree of polymerization of from 500-10,000 to form a mixture,
(ii) adding a surfactant to the mixture, and
(iii) adding water and mixing to form an oil-in-water emulsion, wherein the mixture of the carrier fluid, the SiH-containing organopolysiloxane and the alkenyl-containing organopolysiloxane forms an oil phase of the oil-in-water emulsion; and
(B) reacting the SiH-containing organopolysiloxane and the alkenyl-containing organopolysiloxane in the oil phase of the emulsion formed in (A)(iii) in the presence of a hydrosilylation catalyst to form an emulsion of a silicone fluid that does not comprise gels and has pituitous rheological properties and wherein the emulsion comprises from 40 to 95 wt % of said silicone fluid.

2. The method of claim 1, wherein the alkenyl-containing organopolysiloxane is vinyl terminated.

3. The method of claim 1, wherein the alkenyl-containing organopolysiloxane is dimethyl vinyl terminated.

4. The method of claim 1, wherein the SiH-containing organopolysiloxane has 2 to 10 pendant SiH sites.

5. The method of claim 1, wherein the oil phase comprises from 40% to 80% by weight of the emulsion formed in (A)(iii).

6. The method of claim 1, wherein the surfactant is non-ionic, cationic, or anionic.

7. The method of claim 6, wherein the surfactant comprises from 0.01% to 10% by weight of the emulsion formed in (A)(iii).

8. The method of claim 1, wherein the molar ratio of vinyl:SiH is from 0.01 to 10.

9. The method of claim 1, wherein the carrier fluid comprises 5% to 80% by weight of the emulsion of a silicone fluid having pituitous rheological properties.

10. The method of claim 1, wherein the carrier fluid is a silicone fluid, an organic solvent, an organic oil, or any combination thereof.

11. The method of claim 1, wherein the silicone fluid comprises a branched organopolysiloxane.

12. The method of claim 1, where the pituitous rheological properties of the silicone fluid are determined from a plot of normal stress in Pascals vs a perpendicular shear rate in sec-1 wherein the plot has an average slope that is greater than 3.6.

13. The method of claim 1, wherein the emulsion of a silicone fluid having pituitous rheological properties further comprises a silicone resin and/or silicone elastomer.

14. The method of claim 1, wherein the emulsion comprises from 50 to 95 wt % of said silicone fluid.

15. The method of claim 1, wherein the emulsion comprises from 60 to 95 wt % of said silicone fluid.

16. The method of claim 1, wherein the linear SiH-containing organopolysiloxane and linear an alkenyl-containing organopolysiloxane both have less than 0.1 wt % of T and Q units.

17. The method of claim 1, wherein the linear SiH-containing organopolysiloxane has a degree of polymerization of from 25-400.

18. The method of claim 1, wherein the alkenyl-containing organopolysiloxane is linear and has less than 1 wt % of T and Q units.

* * * * *